US006894153B1

(12) United States Patent
Kotaki et al.

(10) Patent No.: US 6,894,153 B1
(45) Date of Patent: May 17, 2005

(54) GENE ANY-RF; DORMANCY REGULATORY SUBSTANCE, PROCESS FOR PRODUCING THE SAME AND CELL REGULATOR FOR VITAL CELLS

(75) Inventors: Toyomi Kotaki, Ibaraki-ken (JP); Masuhiro Tsukada, Ibaraki-ken (JP); Koichi Suzuki, Iwate-ken (JP); Ping Yang, Iwate-ken (JP)

(73) Assignee: National Institute of Agrobiological Sciences, Ibaraki-Ken (JP)

( * ) Notice: Subject to any disclaimer, the term of this patent is extended or adjusted under 35 U.S.C. 154(b) by 0 days.

(21) Appl. No.: 09/674,436

(22) PCT Filed: May 26, 2000

(86) PCT No.: PCT/JP00/03388

§ 371 (c)(1),
(2), (4) Date: Jul. 16, 2001

(87) PCT Pub. No.: WO00/73441

PCT Pub. Date: Dec. 7, 2000

(30) Foreign Application Priority Data

May 31, 1999 (JP) ............................................. 11-152273
Mar. 22, 2000 (JP) ....................................... 2000-081012

(51) Int. Cl.[7] ....................... C12N 15/12; C07K 14/435; C07K 1/16; A61K 38/02; C12P 21/02
(52) U.S. Cl. ...................... 536/23.1; 530/344; 530/330; 530/343; 512/2; 435/69.1
(58) Field of Search ............................... 530/343, 344; 536/23.1; 435/69.1

(56) References Cited

FOREIGN PATENT DOCUMENTS

| EP | 0 502 696 A1 | | 9/1992 |
|---|---|---|---|
| WO | WO 94/03205 | * | 2/1994 |
| WO | WO 95/13393 | * | 5/1995 |
| WO | WO 95/20661 | * | 8/1995 |

OTHER PUBLICATIONS

Burgess et al., J of Cell Bio. 111:2129–2138, 1990.*
Lazar et al Molecular and Cellular Biology 8:1247–1252 1988.*
Bowie et al. Science, 247:1306–1310, 1990.*
Freshney (Culture of Animal Cells, A Manual of Basic Technique, Alan R. Liss, Inc., 1983, New York, p. 4).*
Steveson et al (2003, Endocrinology, vol. 144, pp. 188–200).*
Darnell et al (1990, Molecular Cell Biology, p. 344 only).*
Gura (Science, 1997, 278:1041–1042).*
Curti (Crit. Rev. in Oncology/Hematology, 1993, 14:29–39).*
Dermer (Bio/Technology, 1994, 12:320).*
Suzuki, et al.: J. Insect Physiol., 36, 855–860, 1990, "Control Mechanism of Diapause of the Pharate First–Instar Larvae of the Silkmoth".

Naya et al., wild Silkmoth & Silk I, 195–200, 1994: Identification of a Maturation Factor Inducing Post–Diapause Development in Pharate First–Instar Larvae of the Wild Silkmoth, Antherae yamamai.

Imai et al., Proc. Japan Acad., 67B, 98–101, 1991; "Isolation and Structure of Diapause Hormone of the Silkworm, Bombyx mori".

Kondo, et al., J. biol. Chem . . . , 267, 473–478, 1992: "Identification of Novel Blood Proteins Specific for Mammalian Hibernation".

Bulletin of the Sericultural Experiment Station, vol. 12, pp. 393–481, Jan. 1946.

Yoshichiro Umeya: Studies on Embryonic Hibernation and Diapause in Insects, Proc. Japan Acad., 26. 1–9 (1950).

Stanley D. Beck, "Insect Photoperiodism" pp. 288, Academic Press, London (1968).

Japanese Document vol. 28: 810–819 (1990) (Kondoh, T. Biological Clock of Plants, Kagakuto Sei Butsu (Chemistry and Biology).

Japanese Document pp. 159, 1995 (Kawashima, S. (ed.) Endocrinology).

Koyama, et al., Japan J. Cancer Res., 87, 1259–1262, 1996, "Presence in *Pieris rapae* of Cytotoxic Activity against Human Carcinoma Cells".

Suzuki, et al., Int. Society for wild silkmoth, 79–84, 1989: "Artificial Hatching in the Silkworr, *Antheraea yamamai*: application of KK–42 and its analogs".

(Continued)

Primary Examiner—Larry R. Helms
Assistant Examiner—Misook Yu
(74) Attorney, Agent, or Firm—Arent Fox

(57) ABSTRACT

The present invention provides a gene Any-RF derived from an insect, having dormancy-control activity and biological cell-control function; a dormancy-control substance and a method for preparing the same; as well as a biological cell-control agent, which comprises, as an effective component, a physiologically active substance having a biological cell-control function and which never causes any antigen-antibody reaction in the living body.

The gene encodes for a protein having an amino acid sequence specified as Sequence No. 1 in SEQUENCE LISTING: Asp-Ile-Leu-Arg-Gly, whose C-terminal is amidated and having a molecular weight of 570.959. The physiologically active substance comprising such a gene is a peptide, which can be isolated and purified by adding an acid-methanol aqueous solution to *Antheraea yamamai*, triturating the resulting mixture, centrifuging the same and then treating the resulting supernatant in an HPLC system. The peptide permits the control of the dormancy of insects and is also useful as a biological cell-control agent, which comprises, as an effective component, such a peptide.

12 Claims, 12 Drawing Sheets

OTHER PUBLICATIONS

Moore, et al., Peptide Research, 7, 265–265 1994: "Preliminary Experimental Anticancer Activity of Cecropins".

Winder, et al.: Biochem biophys Res Commum, 242, 608–612, 1998: "Expression of Antimicrobial Peptides Has an Antitumor Effect in Human Cells".

Kono, et al.: Proc. Japan Acad., 73B, 192–194, 1997: "Anti–cancer Substance in *Pieris brassicae*".

Watanabe, et al.: Japan J. Cancer Res., 89, 556–561, 1988: "Purification of Pierisin, an Inducer of Apoptosis in Human Gastric Carcinoma Cells, from Cabbage Butterfly, *Pieris rapae*".

\* cited by examiner a : Reverse phase HPLC pattern observed for the precipitates obtained after the treatment with a 80% acetone solution, using TSKgel ODS-80Ts column b : Acetonitrile concentration in a 0.1% TFA aqueous solution c : Active fractions of repressive factor

- a : Reverse phase HPLC pattern observed for the active fraction recovered through the 1st HPLC(FIG.2), obtained using TSKgel ODS-80Ts column
- b : Acetonitrile concentration in a 0.1% TFA aqueous solution
- c : Active fractions of repressive factor a : HPLC pattern observed for the active fraction
    recovered through the 2ⁿᵈ HPLC(FIG.3), obtained
    using Rspak NN-614 column b : Acetonitrile concentration in a 0.1% TFA aqueous
    solution c : Active fractions of repressive factor (A)   (B)

SEQUENCE LISTING

```
<160> NUMBER OF SEQ ID NOS: 7

<210> SEQ ID NO 1
<211> LENGTH: 5
<212> TYPE: PRT
<213> ORGANISM: Artificial Sequence
<220> FEATURE:
<223> OTHER INFORMATION: Synthesized peptide

<400> SEQUENCE: 1

Asp Ile Leu Arg Gly
                5

<210> SEQ ID NO 2
<211> LENGTH: 4
<212> TYPE: PRT
<213> ORGANISM: Artificial Sequence
<220> FEATURE:
<223> OTHER INFORMATION: Synthesized peptide

<400> SEQUENCE: 2

Ile Leu Arg Gly

<210> SEQ ID NO 3
<211> LENGTH: 7
<212> TYPE: PRT
<213> ORGANISM: Artificial Sequence
<220> FEATURE:
<223> OTHER INFORMATION: Synthesized peptide
<220> FEATURE:
<221> NAME/KEY: Acp
<222> LOCATION: 2
<223> OTHER INFORMATION: epsilon 6-aminocaproic acid
<220> FEATURE:
<221> NAME/KEY: Amidation
<222> LOCATION: 7
<223> OTHER INFORMATION: Amidated glycine

<400> SEQUENCE: 3

Cys Xaa Asp Ile Leu Arg Xaa
```

```
                                        -continued
                          5

<210> SEQ ID NO 4
<211> LENGTH: 4
<212> TYPE: PRT
<213> ORGANISM: Artificial Sequence
<220> FEATURE:
<223> OTHER INFORMATION: Synthesized peptide
<220> FEATURE:
<221> NAME/KEY: Amidation
<222> LOCATION: 4
<223> OTHER INFORMATION: Amidated phenylalanine

<400> SEQUENCE: 4

Phe Met Arg Xaa

<210> SEQ ID NO 5
<211> LENGTH: 5
<212> TYPE: PRT
<213> ORGANISM: Antheraea yamamai Guerin-Meneville
<220> FEATURE:
<221> NAME/KEY: Amidation
<222> LOCATION: 5
<223> OTHER INFORMATION: Amidated glycine

<400> SEQUENCE: 5

Asp Ile Leu Arg Xaa
                  5

<210> SEQ ID NO 6
<211> LENGTH: 4
<212> TYPE: PRT
<213> ORGANISM: Artificial Sequence
<220> FEATURE:
<223> OTHER INFORMATION: Synthesized peptide
<220> FEATURE:
<221> NAME/KEY: Amidation
<222> LOCATION: 4
<223> OTHER INFORMATION: Amidated glycine

<400> SEQUENCE: 6

Ile Leu Arg Xaa

<210> SEQ ID NO 7
<211> LENGTH: 5
<212> TYPE: PRT
<213> ORGANISM: Chloridea obsoleta Fabricius and Sideridis unipuncta
      Haworth
<220> FEATURE:
<221> NAME/KEY: Unknown amino acid
<222> LOCATION: 2
<223> OTHER INFORMATION: Unknown amino acid
<220> FEATURE:
<221> NAME/KEY: Amidation
<222> LOCATION: 5
<223> OTHER INFORMATION: Amidated Leu

<400> SEQUENCE: 7

Phe Xaa Pro Arg Xaa
                  5
```

GENE ANY-RF; DORMANCY REGULATORY SUBSTANCE, PROCESS FOR PRODUCING THE SAME AND CELL REGULATOR FOR VITAL CELLS

TECHNICAL FIELD

The present invention relates to a gene Any-RF, a substance for controlling dormancy (a dormancy-control substance) and a method for preparing the same as well as a cell-control (inhibition) agent for biological cells and more specifically to a gene Any-RF derived from insects in their pre-larval forms and having a dormancy-control activity and a biological cell-control function, a dormancy-control substance from insects in their pre-larval forms and a method for preparing the same as well as a cancer cell growth-controlling agent. In this specification, the gene which is isolated and purified by the present invention and encodes a specific protein is named "Any-RF" and will hereunder be abbreviated as "gene Any-RF" according to need.

BACKGROUND ART

Conventionally, it has not yet been known that there is a gene derived from an insect and possessing the dormancy-control activity and that such a gene exhibits a biological cell-control function. We will hereunder describe the peripheral techniques of the dormancy-control activity and biological cell-control function, in order to make the understanding of the present invention easy.

Various kinds of and diversity of insects, which have been said to be on the order of 1,000,000 kinds, forcefully and vigorously inhabit the earth under the all sort of environments. These insects live in almost whole areas on the earth including the tropics, the temperature regions, the coniferous forest regions, the ice and snow regions and the deserts as well as the lakes and marshes, while they are adapted to the environments of these regions. Such a phenomenon would be nothing but the fact that the insects certainly acquire diversified functional characteristics required for forcefully living or surviving in the all sorts of environments. We would gain a great deal of information from the insect kingdom. The functional characteristics of the insect include, for instance, biophylaxis mechanisms, growth- and development-control mechanisms, wide variety of natural and synthetic substance-decomposition and—production abilities, sharp sensory functions, behavior-control mechanisms, brain-nerve mechanisms, intermediation functions or environment-adapting ability.

We can obtain valuable information, which would be useful for establishing up-to-date and creative new technologies in the future, by analyzing the environment-adaptive and energy-saving functions of these insects. Moreover, the development of a technique, which makes the most use of physiologically active substances possessing diversified functions and derived from insects, by analyzing the functions of insects would be quite significant for the human beings. Physiologically active substances, which are isolated from insects and whose structures are identified, are also quite significant as subjects of researches for developing high quality and novel products in the fields of, for instance, agriculture and medical and pharmaceutical products.

First of all, we will hereunder describe the dormancy-control function of the insect.

The insect possesses diversified functional characteristics and, in particular, the dormancy function of the insect can be said to be a noteworthy function as an admirable environment-adapting phenomenon. The meaning of the scientifically inspecting for the dormancy of the insect is as follows:

(1) The dormancy is a phenomenon in which an organism completely stops its growth during the growing process and can be interpreted as an energy-saving biological phenomenon for overcoming the unexpected harmful environments such as high temperature or low temperature seasons and/or a shortage of provisions (or food shortage).

(2) The dormancy is a phenomenon in which the organism stops its growth, in advance, through genetic control before the life of the organism is adversely affected by the living environment or through the decoding of the environmental information. Therefore, it would be recognized as a positive strategy for the environmental adaptation unlike the simple interruption of the development.

(3) If the dormancy can be controlled, such a technique may be practically quite important for the control of harmful insects and for promoting the germination of crop seeds and it would be an applied technique in the field of agriculture.

Accordingly, if the mechanism of the dormancy control in the insect is clearly elucidated, the structure of any dormancy-control substance is determined and the functions of the substances are elucidated, the results thus obtained can be applied to the biological industries. More specifically, the results permit the free control of the growth and development of an organism valuable for the human beings and also permit the interruption of the living activities of organisms harmful to the human beings by arbitrarily inducing the dormancy of the organisms. Consequently, the dormancy control would be an important basic research from the viewpoint of the biological industries in the 21st century. In addition, the elucidation of the functions of dormancy-control substances would be quite important for the development of high quality and novel products effective in the fields of agriculture and medical and pharmaceutical products.

For instance, an *Antheraea yamamai* as a kind of the insects belonging to Lepidoptera falls into-dormancy in the beginning of autumn like a variety of other insects and awakes from the dormancy in April or May after staying over the winter season, in the state of dormancy. The *Antheraea yamamai* apparently has embryonic diapause in the egg state like the silkworm, but the larva body is almost completely formed in the egg and it falls into dormancy in this condition. Accordingly, the dormancy of this type is recognized to be a kind of the dormancy in the pre-larval state (also called "pre-larval dormancy"). There have been known not less than 40 kinds of insects falling within those of this type, represented by Lepidoptera such as gypsy moth in addition to the *Antheraea yamamai* and thus they should be classified as a new dormancy type one. In this respect, there has been proposed such a model that the central hormone system of the insect is not directly involved in the pre-larval dormancy of the *Antheraea yamamai*, but the pre-larval dormancy is controlled by the repressive factor (RF) present in the mesothorax site of the insect and that the post-larval dormancy thereof is controlled by the maturation factor (MF) present in the 2nd to 5th abdominal segments (Suzuki et al., J. Insect Physiol., 1990, 36:855–860, the disclosure of which is hereby incorporated by reference herein). The maturation factor is partially purified and is reported to be a peptide-like hormone (Naya et al., Int. Wild Silkmoth & Silk 1, 195–200, 1994, the disclosure of which is hereby incorporated by reference herein), but the repressive factor (dormancy-control substance) has not yet been isolated at all.

In addition, in respect of the silkworm, which falls into embryonic diapause, a dormancy-inducing hormone (generally, called diapause hormone) is known as an induction hormone and the hormone is a peptide hormone comprising 24 amino acid residues and having a C-terminal amide group (Imai et al. Proc. Japan. Acad., 1991. 67B: 98–101, the disclosure of which is hereby incorporated by reference herein). In the case of the insects, which fall into embryonic diapause, however, the presence of any hormone other than the foregoing one involved in the dormancy has not yet been confirmed at all. On the other hand, in the case of the insects, which have pre-larval dormancy, any dormancy-related hormone substance has not yet been discovered at all.

Other than the insect, three kinds of substances called hibernation-specific proteins are isolated from the chipmunk (Kondo et al., J. Biol. Chem., 1992, 267: 473–478, the disclosure of which is hereby incorporated by reference herein). However, these proteins have high molecular weights on the order of 27, 25 and 20 K, respectively, the blood concentrations thereof before the hibernation are lower than those observed after the hibernation and they are low during the hibernation. Moreover, there has not yet been discovered any dormancy-control substance in any mammal. For instance, in case of the embryonic diapause of the wallaby (a kind of kangaroo), the maternal pineal body thereof is considered to be involved in the dormancy, but any dormancy-control substance has not yet been isolated at all.

As has been discussed above, there has not yet been isolated, from the insect, any gene encoding a protein having a dormancy-control activity and/or any useful dormancy-control substance having a dormancy-control activity. Moreover, the hibernation-specific proteins isolated from the chipmunk suffer from such problems that they have high molecular weights and accordingly, they are liable to cause antigen-antibody reactions and that the blood concentrations of the proteins vary before and after the hibernation and they are low during the hibernation. Furthermore, there has not yet been discovered any dormancy-control substance in the mammal. Consequently, the development of a substance having a dormancy-control activity has presently been desired from the considerably wide viewpoint, including the dormancy control of the insect and the dormancy-control and growth-control of the mammal whose dormancy phenomenon has been confirmed.

Up to now, in the case of the insects, the dormancy has been classified into egg diapause, larval dormancy, pupal diapause and imaginal dormancy. However, the dormancy stage is quite complicated as will be detailed below, from the physiological-biochemical standpoint and therefore, this dormancy stage (i.e. the pre-larval dormancy stage) should endocrinologically be classified as a new stage. More specifically, there have been known insects, such as the *Antheraea yamamai* which does not belong to the group simply falling into the egg diapause but uniquely falls into the dormancy in the pre-larval stage and the aspen sawfly (*Trichiocampus populi* Okamoto) which does not belong to the group falling into the pupal diapause but belong to the group falling into the dormancy in the pre-pupal stage prior to the pupal stage. Therefore, it may be expected that the insects of these kinds include novel dormancy-control hormones and substances related thereto.

There has not yet been isolated any dormancy-control substance, which acts on not less than 40 kinds of insects represented by Lepidoptera such as *Antheraea yamamai*, gypsy moth, pellucid white butterfly, tent caterpillar (*Malacosoma neustria testacea* Motschulsky) and daimyo oak tussock moth (*Liparis aurora* Butler), which belong to the group falling into pre-larval dormancy (these insects of the pre-larval dormancy type are disclosed in the article of UMEYA Y., entitled "The Hibernation Phenomena in Egg State of Insects, Based on the Hibernating Egg of Silkworm", Bulletin of the Sericultural Experiment Station (Reports from the Sericulture Experiment Station), 1946, 12: 393–481 and UMEYA Y., "Studies on embryonic hibernation and diapause in insects", Proc. Jpn. Acad., 1950, 26: 1–9, the disclosure of which is hereby incorporated by reference herein). There has thus been strongly desired for the isolation and identification of such a dormancy-control substance, in the fields of agriculture, forestry and pharmaceutical products, and it has also been desired for the development of a manufacturing technique for economically and efficiently preparing such substances.

The original country of the *Antheraea yamamai* (formal Japanese name: YAMAMAYU; technical name: *Antheraea yamamai* Guerin-Meneville) is Japan, the rearing of the silkworm was put on record in the EDO era and has a long history. The rearing of the larvae thereof has recently become easy due to the development of artificial feeds therefor. In addition, they are in general reared in farmhouses and there are a great deal of information concerning the rearing thereof and they can easily be available. The silkworm breeds once a year and hibernates in the egg state. The larvae of the domestic silkworm *Bombyx mori* (Japanese name: "KAIKO") exclusively eat mulberry leaves, while those of the *Antheraea yamamai* eat leaves of, for instance, *Quercus acutissima, Quercus serata* Thunb, *Quercus dentata* Thunb and *Quercus variabilis* Blume. The silkworm-raising farmer breeds the larvae of the domestic silkworm, while the larvae of the wild *Antheraea yamamai* ("YAMAMAYU") naturally breed and grow. The hatchability of the *Antheraea yamamai* is very low, the rate of the silk yarn recovered from the cocoon yarn (yarn yield) is very low and the operations for recovering the cocoon yarn are quite difficult. Accordingly, the recovery thereof is very significant and has high rarity value. The value of silk yarn derived from the *Antheraea yamamai* is estimated at 200,000 yen or even 300,000 yen per unit kg thereof and the yarn thus has rarity value to such an extent that it is referred to as "Silk diamond". In the silk fabric whose rate of silk yarn derived from *Antheraea pernyi* (i.e. the wild silkworm) incorporated is high, the slippage of the yarn is inhibited and the resistance to slip-down of seams can be improved and accordingly, such fabrics have preferably been used. For this reason, the future development in the fields, which make use of the *Antheraea yamamai* or a large silk yarn-producing insect, will greatly be expected. Therefore, it has increasingly become important to isolate repressive factors concerning the control of the living environment for the *Antheraea yamamai* and to determine the structure thereof.

The reason why the dormancy-control substance of the *Antheraea yamamai* has not yet conventionally been able to be identified would be as follows: The presence of dormancy-control substances has been predicted in 1990 (Suzuki et al., J. Insect Physiol., 1990, 36: 855–860, the disclosure of which is hereby incorporated by reference herein), but it took a great deal of time to improve extraction methods and to select columns for the purification and accordingly, such predicted active fractions could not be isolated and purified. A principal reason for this is that the substances to be identified are short peptides each having a very low molecular weight (hereunder also referred to as "low molecular weight peptides" and it has been unexpectedly difficult to extract them and to select an appropriate extraction column. For this reason, there have presently been desired for the establishment of a method for purifying these substances, which is required for the isolation of such dormancy-control substances from the pre-larvae and is excellent in the yield, efficiency and production cost, and can easily be operated.

Next, we will describe substances derived from insects and possessing cell growth-inhibitory functions. As physiologically active substances derived from insects, there have been known so-called living body-protective (biophylaxis) substances or antibacterial peptides, there are as many as not less than 150 kinds of such peptides and most of them have been isolated and the structures thereof have been determined. However, it is not very long since novel substances derived from insects and having anti-tumor activities were discovered and accordingly, there has been only a small amount of information concerning these novel substances.

An example of carcinostatic substances derived from insects is a peptide called Cecropin. This peptide is one isolated from Cecropia silkworm and whose structure is determined. After the determination of the structure, a variety of substances each having a structure similar to that of Cecropin have been isolated from a variety of insects and identified. It is reported that Cecropin has anti-tumor activity to cultured cells of lymphoma and leukemia (Moore, A. et al., Peptide Res., 1994, 7: 265–269, the disclosure of which is hereby incorporated by reference herein). Moreover, it is confirmed that the gene coding for Cecropin is genetically recombined into the cultured cell derived from human bladder cancer and the resulting recombined cells are injected into a nude mouse and as a result, it was found that the cells could inhibit any growth of the tumor cells (carcinostatic effect) (Winder, D. et al, Biochem. Biophys. Res. Commun., 1998, 242: 608–612, the disclosure of which is hereby incorporated by reference herein).

It is also reported that the high molecular weight protein isolated from a chrysalis of cabbage butterfly possesses strong cytotoxic activity to cancer cells such as human gastric carcinoma cells (TMK-1), can inhibit any growth of the cancer cells and ultimately exhibits such a specific physiological activity that it induces apoptosis, this protein being named Pierisin (Koyama et al., Jpn. J. Cancer Res., 1996, 87: 1259–1262; Kono et al., 1997; Watanabe et al., 1998, the disclosure of which is hereby incorporated by reference herein). This cytotoxicity finally induces apoptosis (death of cells) and accordingly, clearly indicates that the protein surely exhibits carcinostatic activity.

The protein (Cecropin) isolated from the Cecropia silkworm and the protein (Pierisin) isolated from the chrysalis of cabbage butterfly, described above, are high molecular weight physiologically active substances having molecular weights of about 4 K and 98 K, respectively. These known physiologically active substances can effectively reduce the cancer cells by inducing apoptosis in the living cancer cells, but they suffer from a problem in that it is impossible to certainly change the stage of cancer cell cycles and to thus once maintain the cancer cells in their intermitotic state (i.e. the resting cancer cells). In addition, the application of Cecropin or the like to the living body is not desirable from the practical standpoint although there has been reported that Cecropin can inhibit any growth of human cancer cells. This is because a high molecular weight protein causes an antigen-antibody reaction in the living body.

Under such circumstances, there has strongly been desired for the development of a substance capable of inhibiting any growth of cancer cells, which is a physiologically active substance derived from an insect, which has a biological cell-control function such as a cancer cell growth-inhibitory function and which never causes any antigen-antibody reaction when it is administered to a living body.

DISCLOSURE OF THE INVENTION

Accordingly, it is an object of the present invention to provide a gene Any-RF derived from insects, a dormancy-control substance and a method for preparing the same as well as a cell-control agent (such as cancer cell growth-control agent) for biological cells, comprising as an effective component a physiologically active substance which has a cell-control function (such as a cancer cell growth-inhibitory function) in biological cells and which never causes any antigen-antibody reaction in the living body. To this end, a gene: Any-RF possessing a dormancy-control activity and a cell-control function in biological cells, a dormancy-control substance and a biological cell-control agent are efficiently and economically isolated from the pre-larval body of an insect, followed by identification and purification thereof.

The gene Any-RF according to the present invention codes for a protein, which has an amino acid sequence: Asp-Ile-Leu-Arg-Gly (SEQ ID NO:1), which has a C-terminal amide group (SEQ ID NO:5) and which has a molecular weight of 570.959; possesses dormancy-control activity and is derived from the pre-larvae of *Antheraea yamamai*.

The dormancy-control substance according to the present invention has an amino acid sequence: Asp-Ile-Leu-Arg-Gly (SEQ ID NO:1), has a C-terminal amide group (SEQ ID NO:5) and has a molecular weight of 570.959.

The dormancy-control substance of the present invention can be prepared as follows. For instance, an acid-methanol solution consisting of methanol: water: acetic acid is added to pulverized pre-larvae of an insect belonging to Lepidoptera such as the pre-larvae of *Antheraea yamamai*, then the resulting mixture is triturated in a mortar, followed by centrifugation of the triturated mixture and introduction of the resulting supernatant into an HPLC system, which comprises a reverse phase high performance, liquid chromatography and a mixing-separating mode high performance liquid chromatography, to thus isolate and purify the intended substance. Alternatively, the dormancy-control substance can likewise be prepared by any known method using a known peptide synthesis device.

If the dormancy-control substance comprising the gene Any-RF according to the present invention is administered to, for instance, pre-larvae, during their dormancy, whose growth is destined to have dormancy and to awake, the destined dormancy and awakening can be extended or stopped. For this reason, if the dormancy-control substance of the present invention is administered to an organism, which has been confirmed to have dormancy, the life mechanism of such a low energy metabolism as the essence of the dormancy of the organism can thus be elucidated. This substance may ultimately serve as a leading compound for the development of a substance capable of extending the span of life.

Since the dormancy-control substance of the present invention is a low molecular weight peptide, it does not easily cause any antigen-antibody reaction even when externally administered to a living body and has particularly excellent growth-inhibitory activity. Therefore, the substance having such a structure can directly be administered to a variety of organisms, which fall into dormancy, without any modification. Moreover, a variety of possible functions can easily be examined and studied by externally administering a synthetic peptide having a structure identical to that of the low molecular weight peptide.

In addition, the living cell-control agent according to the present invention, for instance, a cancer cell growth-inhibitory agent comprises, as an effective component, a peptide, which has an amino acid sequence: Asp-Ile-Leu-Arg-Gly (SEQ ID NO:1), which has a C-terminal amide group (SEQ ID NO:5) and which has a molecular weight of 570.959. This peptide is one derived from the pre-larvae of *Antheraea yamamai* as already discussed above and can be prepared by the same method used above.

Furthermore, the living cell-control agent according to the present invention, for instance, a cancer cell growth-inhibitory agent may be one comprising, as an effective component, a peptide having an amino acid sequence: Ile-Leu-Arg-Gly (SEQ ID NO:2), which corresponds to that specified as SEQ ID NO:1 from which the N-terminal Asp residue is deleted, which has a C-terminal amide group (SEQ ID NO:6) and which has a molecular weight of 456.58.

The peptide as the physiologically active substance according to the present invention is a penta-peptide comprising 5 amino acid residues (molecular weight: 570.595) or a tetra-peptide (molecular weight: 456.58) comprising 4 amino acid residues. Therefore, the peptide of the present invention hardly causes any antigen-antibody reaction, as compared with Cecropin (molecular weight: about 4 K) derived from silkworm and Pierisin (molecular weight: 98 K) derived from cabbage butterfly, even when administered to the living body, and possesses quite remarkable carcinostatic activity. Thus, such a low molecular weight peptide as that of the present invention can directly and externally be administered to not only human, but also other higher animals such as domestic animals without any modification and the administration thereof makes the peptide show its anticancer function.

Moreover, the peptide or the physiologically active substance according to the present invention may likewise be a novel medical agent having a cell growth-control effect and free of any antigen-antibody reaction. The low molecular weight peptide comprising the gene Any-RF according to the present invention has such a function that it can efficiently inhibit any growth of the cancer cells without accompanying any side effect. Therefore, the peptide can efficiently inhibit any cell growth in, for instance, human hysterocarcinoma, hepatoma, lung cancer, gastric carcinoma and breast cancer and in its turn, efficiently controls biological cells.

This physiologically active substance has a marked characteristic in that it serves not to increase the number of living cells of cancer cells and makes the surviving cancer cells change the cell cycle thereof to thus once maintain the cancer cells in their intermitotic state. In this respect, the physiologically active substance of the present invention differs from any conventional carcinostatic agent in the mechanism of action and is quite useful as a medicine. More specifically, the physiologically active substance according to the present invention can reduce the S phase (stage), which correspond to DNA-replication phase, while it can serve to extend the G0 phase corresponding to the resting period and the G1 phase corresponding to the first stage. Contrary to this, either Cecropin or Pierisin simply serves to inhibit any growth of cancer cells by reducing the number of living cells and to suppress the growth of the cancer cells by inducing a harmful effect (apoptosis) on the normal cells. Accordingly, the physiologically active substance of the present invention cell solve such a problem associated with the conventional carcinostatic agents including the foregoing Cecropin and Pierisin as the apoptosis against the normal cells has such an excellent effect that it does not adversely affect most of the normal cells in their resting stage and thus simply inhibits proliferative cells, and as a result, it can efficiently inhibit any proliferation of cancer cells.

In general, it has been said that the G0 and G1 phases take the longest period in the cell cycle. The physiologically active substance of the present invention, which serves to increase the both stages, fundamentally differs from the conventionally reported substances derived from insects and having a cancer cell-control effect. The conventional carcinostatic agents induce condensation and fragmentation of nuclei accompanied by the apoptosis to thus reduce the number of living cells. However, the physiologically active substance of the present invention serves to extend the G0 and G1 phases in the cell cycle and to shorten the S phase thereof and as a result, the cell cycle of the living cells requires a longer period of time and the growth of the cells is ultimately inhibited. Accordingly, the physiologically active substance of the present invention does not induce the death of cells (apoptosis) in the cancer cell growth, but serves not to increase the number of cells by controlling the cell cycle and in turn inhibiting any growth of the cells.

As has been discussed above, the physiologically active substance of the present invention serves to extend the dormancy phase of the pre-larvae of *Antheraea yamamai*, as one of the physiologically active functions. In general, it has been recognized that the dormancy of organisms is characterized by interruption of the cell proliferation and maintenance of a low energy condition. Therefore, the substance can be utilized in order to control the cancer cell growth in mammals as an example of the applications of the substance having diversified functions. Moreover, the substance may inhibit the growth of a variety of biological cells and accordingly, the substance can be used as a long term preservative for culture cells in the level of cells and individual organisms.

BEST MODE FOR CARRYING OUT THE INVENTION

Figure 1:
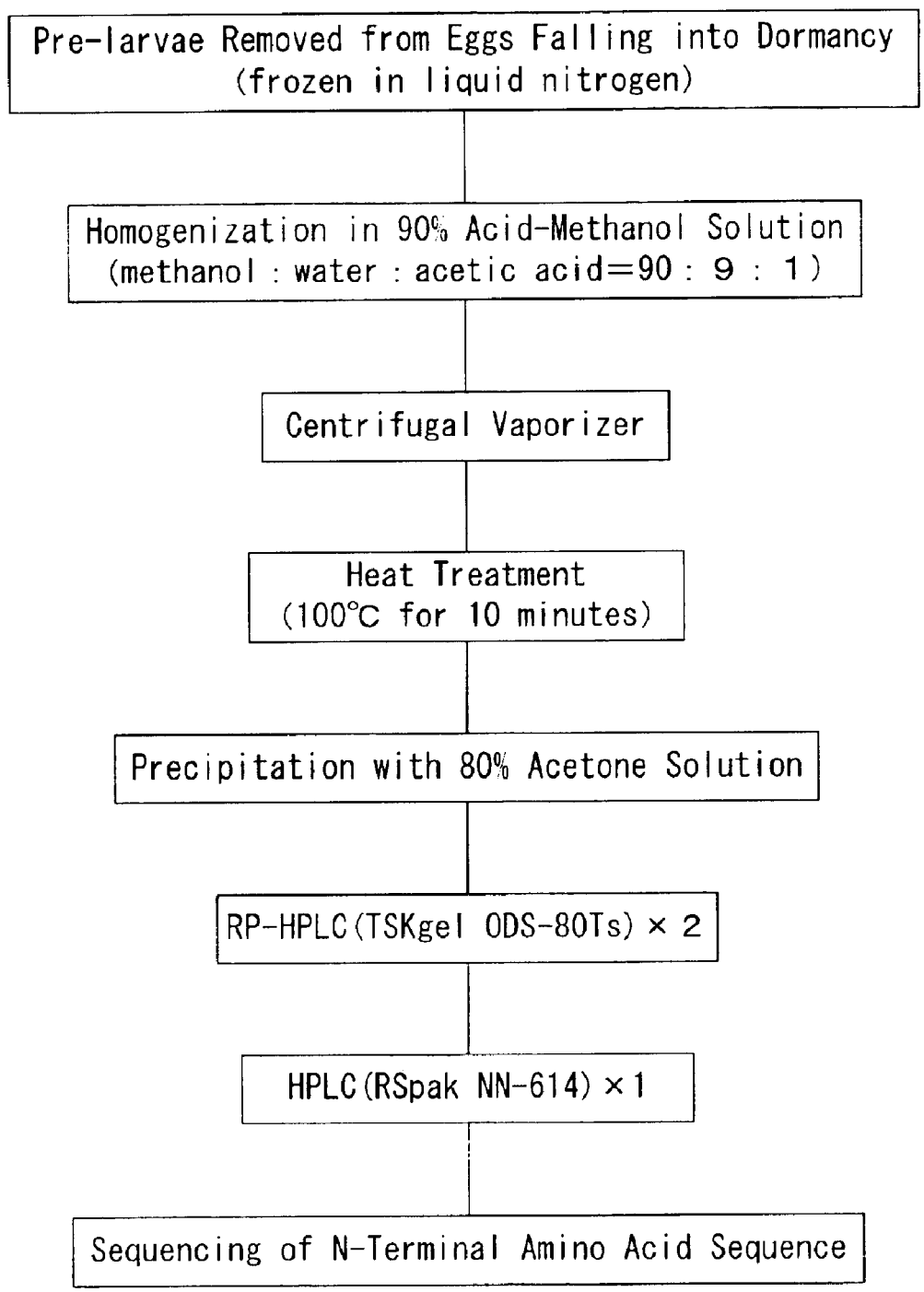
FIG. 1 is a flow sheet for showing the processes for isolating and purifying the dormancy-control substance according to the present invention.

Insects usable in the present invention may be any type of insects, which fall into dormancy in their pre-larvae states and include, for instance, a larva of *Antheraea yamamai*, and larvae of gypsy sawfly, pellucid white butterfly, tent caterpillar (*Malacosoma neustria testacea* Motschulsky) and daimyo oak tussock moth (*Liparis aurora* Butler) as well as larvae of not less than 40 kinds of insects belonging to Lepidoptera, which are worldwide severely harmful insects for the forest; and larvae of insects belonging to Orthopera such as angular-winged grasshoppers. In the present invention, the pre-larvae of *Antheraea yamamai* are conveniently used as target insects for isolating the gene: Any-RF since they are easily available and there has been a great deal of information concerning the rearing thereof. The present invention will hereunder be described while laying stress on the *Antheraea yamamai*. We will first explain the dormancy-control substance and we will then explain the cell-control agent for living cells.

As has been discussed above, the dormancy-control substance according to the present invention is a novel peptide having a dormancy-control function, 5 amino acid residues thereof from the N-terminal are Asp-Ile-Leu-Arg-Gly (SEQ ID NO:1), and it is a low molecular weight substance (molecular weight. 570.959) and does not have a free oxidized C-terminal, but has a C-terminal carrying an amide group (SEQ ID NO:5). This is clear from the fact that only the peptide whose C-terminal carries an amide group possesses such a control function as demonstrated by the biological assay concerning the compounds prepared in Examples as will be described below. This substance can be isolated and purified from, for instance, the pre-larvae of *Antheraea yamamai* or alternatively, it can be synthesized according to the conventional methods since the amino acid sequence thereof is elucidated.

A composition having an amino acid sequence similar to that of the foregoing dormancy-control substance derived from an insect belonging to Lepidoptera such as *Antheraea yamamai* can efficiently control the dormancy of wide variety of insects belonging to Lepidoptera and Orthopera such as those listed above. This is self-evident from the circadian rhythm (biological clock). More specifically, the development phenomena of a variety of organisms such as the reproduction behavior of animals (including the dormancy of kangaroo), the dormancy of insects and the flower bud formation of plants (including dormancy) can be controlled while making use of the circadian rhythm as disclosed in Beck, S.T., Insect Photoperiodism, pp. 288, Academic Press, London (1968) and KONDO Takao, Biological Clock of Plants, KAGAKU TO SEIBUTSU (Chemistry and Biology), 1990, 28: 810–819, the disclosure of which is hereby incorporated by reference herein).

As has been discussed above, the amino acid sequence of the repressive factor of the peptide, which is involved in the maintenance of the dormancy of the pre-larvae of *Antheraea yamamai*, is Asp-Ile-Leu-Arg-Gly-$NH_2$ (SEQ ID NO:5, the peptide of SEQ ID NO:1 having the C-terminal amidated). There has not any known peptide of this type of penta-peptide even when the computer research (BLAST and FASTA) is performed and thus the penta-peptide is a novel peptide having dormancy-control activity in the biological world. This is named *Antheraea yamamai*-Repressive Factor (abbreviation: Any-RF). Nobody has ever discovered the peptide comprising 5 amino acid residues and whose C-terminal carries an amide group in the free state in the biological world till the present invention has been completed. However, the amino acid segments identical to the foregoing one:—Asp-Ile-Leu-Arg-Gly—can be found in the amino acid sequence of several biological proteins. For instance, the amino acid sequence is identical to that found in the putative 22.1 KD protein (193 amino acid residues) of yeast (i.e. the fragment starting from $166^{th}$ to $170^{th}$ amino acid residues) and that found in the precursor (202 amino acid residues) of the human leukemia-inhibitory factor (i.e. the fragment extending from $142^{nd}$ to $146^{th}$ amino acid residues) according to the computer research. However, the functions of the amino acid sequences of these portions have not yet been elucidated at all. In other words, the amino acid sequence in the peptide of the present invention is sandwiched between − and C-terminals, the C-terminal has an amide group and the sequence is thus present in the free state, although the amino acid sequence of the present invention is identical to the fragment present in large protein sequences. Thus, there has never been discovered such an amino acid sequence present in the free state and possessing such a physiological function.

According to the present invention, a novel peptide hormone, which has never been known from the viewpoint of the endocrinology of insect and which can control the dormancy of insects, can be isolated and identified. In addition, the present invention makes, for the first time, the dormancy mechanism of insects clear. Since it has been confirmed that organisms falling into dormancy include not only insects, but also marine organisms, plants and mammals such as a wallaby (a kind of kangaroo), an important clue to the elucidation of the low energy metabolism involved in the life mechanism, which is the essence of these organisms falling into dormancy, can be obtained by the use of the dormancy-control substance according to the present invention. Thus, the substance may be one capable of maintaining the life over a long period of time in the future and it may ultimately serve as a leading compound for the development of a substance capable of extending the span of life.

In addition, the novel peptide of the present invention isolated from the *Antheraea yamamai* is a penta-peptide comprising 5 amino acid residues and thus it hardly causes any antigen-antibody reaction even if it is externally administered to a living body. Furthermore, this peptide can delay the awakening of the *Antheraea* yamamai from its dormancy, whose awakening from the dormancy is completely destined by an artificially synthesized substance for breaking the dormancy (awakening from the dormancy), and possesses growth-control activity to such a high extent that it can reduce the rate of awakening from dormancy. For this reason, it would be self-evident that the peptide can directly be administered not only to different kinds of insects, from the viewpoint of the circadian rhythm of the organisms, but also to marine organisms, plants and mammals, as disclosed in the foregoing articles.

As has been discussed above, an insect can usually be destined to awake from the dormancy by the following two methods:

(1) A method, which can be applied to eggs of insects in any stage during the dormancy, and in which the shell of an egg is removed with a pincette to thus obtain the pre-larva of the insect prior to the dormancy, followed by applying, to the venter of the pre-larva, 0.1 μg/0.5 μl of a solution of an imidazole compound (1-benzyl-5-[(E)-2,6-dimethyl-1,5-heptadienyl] (hereunder referred to as "KK-42")) in acetone; and (2) a method, which is limited in the stage and in which eggs after the oviposition are stored at 25° C. for about one month and then treated at a low temperature ranging from 2 to 5° C. for 2 to 3 months.

In order to make the dormancy-control function clear, it is sufficient to inoculate, with a dormancy-control substance, the pre-larvae which have been destined to awake from the dormancy by either of the foregoing 2 methods and then allowed to stand over 24 hours. For instance, the pre-larvae are percutaneously inoculated, through the cervical region, with aqueous solutions (0.54 μl) having various concentrations prepared by dissolving the dormancy-control substance of the present invention in distilled water, using a glass capillary tube or the aqueous solutions can be orally administered to the pre-larvae.

The dormancy-control substance according to the present invention can be said to be one, which acts, in the case of the insects, as a diversified growth-control substance in wide variety of insects and every stages of these insects. Therefore, the novel peptide according to the present invention is not only a dormancy-control substance for the pre-larvae of insects, but also has an excellent physiological function and serves as a growth-control agent for a wide variety of organisms including other insects and even mammals.

As has been described above, the penta-peptide of the present invention can be expected to show its function at not only the pre-larval stage, but also other stages. In other words, the stage subsequent to the pre-larval stage (larval body is formed within an egg) is in general the larval stage after the hatching. The same substance may likewise he found even in many insects, which fall into dormancy in the larval stage, represented by cabbage armyworm. This is because, it has been well-known that if the kinds of insects and the stages thereof are different, the same hormone shows different functions. For instance, this can be analogized from the fact that the juvenile hormone serves to maintain dormancy and the character of the larva in the case of insects belonging to Lepidoptera (such as the larva of cabbage army worm), while the hormone serves to stimulate the gonad and the lack thereof serves to maintain the dormancy in the case of adult insects belonging to Coleoptera (such as adult of rumex leaf beetle). Therefore, the novel peptide now isolated may act as a diversified growth-control substance in various stages and a wide variety of insects in addition to "KAIKO".

As conventionally known substances involved in the dormancy of insects, there has been reported simply the dormancy hormone of "KAIKO" as has been described above. This is a peptide amide and most of the peptide hormones of insects are classified into this group and it is common for these peptides that the C-terminal carries an amide group, i.e., Phe-X-Pro-Arg-Leu-amide. In other words, it is a member of the FXPRL amide family. However, this dormancy hormone is a hormone involved in the induction of dormancy in "KAIKO" and does not have any dormancy-maintaining function.

In the case of "KAIKO", the dormancy hormone secreted from the subesophageal ganglion of the mother during its mumia phase acts on the ovary to thus determine the dormancy of the embryo in the egg after the subsequent oviposition. In other words, there is a difference between the time at which the dormancy hormone acts on the ovary and the time at which the dormancy practically takes place. On the other hand, the *Antheraea yamamai* is characterized in that the time at which the novel peptide acts is identical to that at which the dormancy is initiated. However, the structure and the function of the novel peptide of the present invention are substantially different from those of the known hormone involved in dormancy.

In addition, since the peptide of the present invention is a kind of oligopeptides comprising 5 amino acid residues, it may serve not only as a dormancy-control or growth-control substance in living things other than the insect, but also as a sleep-control substance for mammals or the like. In particular, in the higher animals, a low molecular weight peptide such as the peptide of the present invention hardly serves as an antigen as has been discussed above and therefore, the peptide may be characterized in that possible functions of an organism can easily be tested and/or studied by externally administering a synthetic peptide to the organism. Moreover, the peptide of the present invention may be a novel medical agent free of any antigen-antibody reaction and having a cell growth-inhibitory effect.

Physiologically active substances for the first time discovered in insects, such as ecdysone and juvenile hormone, which control the molting and metamorphosis of the insects have recently been discovered even in Crustacea (such as crab and lobster or shrimp), Annelida (such as lubworm and earthworm), or plants such as *Podocarpus nakaii* and *Achyranthes fauriei* in addition to insects (KAWASHIMA Seiichiro (ed.), Endocrinology, 1995, pp.159, the disclosure of which is hereby incorporated by reference herein).

Moreover, a hormone involved in dormancy, which has conventionally been known as a hormone for inducing the dormancy in "KAIKO", is recognized to belong to FXPRL amide family, which are found to be present in other insects, for instance, boll worm (*Chloridea obsoleta* Fabricius) and common armyworm (*Sideridis unipuncta* Haworth). If judging from the foregoing facts, it would be highly probable, from the technical standpoint, that the penta-peptide of the present invention can likewise be isolated and identified from insects other than the *Antheraea yamamai*.

Moreover, there is observed, in the *Antheraea yamamai*, a physiological phenomenon called estivation in not only the pre-larval stage, but also the mumia stage and it falls into dormancy around August although the term thereof is short on the order of about one month. The dormancy during the pupal stage of insects would be due to the shortage of the molting hormone (ecdysone). Therefore, it would be highly probable that the penta-peptide now discovered controls not only the mumia diapause of the *Antheraea yamamai*, but also the pupal diapause of other insects such as cabbage butterfly, *Antheraea pernyi* (Japanese name: "SAKUSAN"), *Hyphantria cunea* Drury and *Hericoverpa assulta* Guenee. In other words, the penta-peptide serves to maintain such a specific physiological state as low energy metabolism (i.e., the function of maintaining the dormancy of the pre-larva of *Antheraea yamamai*) and therefore, it shows the same function in the pupal diapause of other insects in which the stage is pupa and the same physiological state is maintained over a long period of time. For this reason, penta-peptides similar to the foregoing one may be isolated from insects falling into pupal diapause such as cabbage butterfly, *Antheraea pernyi*, *Hyphantria cunea* Drury and *Hericoverpa assulta* Guenee. On the other hand, such peptides may also be isolated from these insects in other various stages of the larvae thereof, in addition to those in the pupal diapause stage. In respect of the hormones of insects, as has been described above, if the kinds of insects and the stages thereof are different from each other, hormones having the same structure would show different functions. For this reason, the same penta-peptide and related substances can be isolated from a wide variety of insects and identified as a dormancy-control factor or a growth-control factor.

In the present invention, to isolate and identify a novel peptide from the pre-larval body of *Antheraea yamamai* the pre-larvae are picked out from eggs in the dormancy state and within one month from the oviposition, followed by immediate freezing thereof with liquid nitrogen and then storing them at −80° C. till they are used in the isolation process. In the isolation process, 10 volumes of an acid-methanol solution (for instance, methanol: water: acetic acid=90:9:1) is added to the pre-larvae, followed by trituration in a mortar and then centrifugation at 10,000 g for 30 minutes to give a supernatant, according to the method as disclosed in FIG. 1. These operations are repeated three times, the combined supernatants are concentrated by a centrifugal vaporizer and then the resulting supernatant is introduced into an HPLC system.

The reason for the use of acetic acid in the acid-methanol solution is as follows. This extraction method is used in the extraction of peptide hormones from other insects and the addition of acetic acid thereto permits the inhibition of not less than 90% of the protease activity and the suppression of any decomposition of the peptides to be extracted. Most preferred acid-methanol solution is a 90:9:1 (% by volume) mixture of methanol: water: acetic acid, but is not particularly limited to this mixture.

In this respect, the penta-peptide can be extracted from the whole body of a variety of insects such as those listed above by repeating the same method used above according to the procedures as shown in FIG. 1. If the peptide is directly extracted from the body fluid of the insects, the body fluid is discharged by cutting parts of the biological tissues such as legs of the larval body, followed by mixing, with ice-cooling, a 90% acid-methanol solution prepared by replacing water in the 90:9:1 mixture of methanol: water: acetic acid shown in FIG. 1 with the body fluid and then extraction according to the procedures as shown in FIG. 1.

In the removal of the pre-larvae from the eggs, it is most preferred to use eggs during dormancy within one month after the oviposition. The reason for this is as follows. The degree of the dormancy is high during the term extending from about $10^{th}$ days after the oviposition to $20^{th}$ days after the initiation of the dormancy, but the degree of the dormancy is low as the time further elapses. In the present invention, only a considerably small amount of the dormancy control substance as a hormone-like substance can be ultimately isolated from 1,500 pre-larvae of *Antheraea yamamai*. If estimating from the activity listed in Table 1 and the molecular weight of about 571, it would be concluded that only 21.4 μg of the dormancy-control substance of the present invention is extracted from 1,500 pre-larvae of *Antheraea yamamai*. However, there have not been developed any artificial feed for *Antheraea yamamai* and any technique for improving the oviposition unlike "KAIKO" and therefore, the egg of the silkworm is quite expensive on the order of 5 to 20 yen per egg. Accordingly, it is unfavorable in view of economy and efficiency to prepare the physiologically active substance of the present invention using the silkworms.

In general, key factors in the extraction of a hormone-like substance are the selection of appropriate raw materials, which permit the achievement of a high rate of recovery of the substance and the best choice of a resin to be packed in a column, which permits the efficient separation of the substance. If they can be artificially synthesized, however, nothing can be better than this. On the other hand, the amino acid sequence has been determined as has been described above and therefore, such an active substance having the sequence can economically and efficiently be synthesized according to any conventionally known method.

Alternatively, if a gene encoding the novel peptide can be identified, the novel peptide may be used in wide variety of biologically industrial fields including not only insects, but also many other kinds of organisms and the growth of these organisms can be controlled at will. Thus, the gypsy moth, which never falls into dormancy, can be constructed by a method comprising the step of incorporating, into the same, an anti-sense gene recombinant of this peptide or a gene as a counterpart of the peptide-encoding gene to thus inhibit the expression of the original gene. If the resulting gypsy moth is released into the natural world, the population thereof on the earth can substantially be reduced and this would economically greatly contribute to the forestry in the North America. Moreover, if the peptide is used as an additive for culture media for cultivating a variety of cells, the cultured cells can be stored over a long period of time. This accordingly leads to the development of a long term preservative for cultured cells and ultimately, this would be a central technique for the development of a long term preservative for cultured cells of insects.

Now, we will hereunder describe the biological cell-control agent of the present invention.

As has been discussed above, the present invention relates to a physiologically active substance having dormancy-control activity, which specifically and efficiently acts on not less than 40 kinds of various insects represented by Lepidoptera such as *Antheraea yamamai*, gypsy moth, pellucid white butterfly, tent caterpillar (*Malacosoma neustria testacea* Motschulsky) and daimyo oak tussock moth (*Liparis aurora* Butler) and Orthopera, which belong to the group falling into pre-larval dormancy. Further the inventors of this invention have found that this physiologically active substance possesses efficient biological cell-control activity, for instance, efficient cancer cell growth-inhibitory activity. More specifically, we have found that the foregoing gene: Any-RF encodes for a protein, which has an amino acid sequence specified as Sequence No. 1 in Sequence Listing: Asp-Ile-Leu-Arg-Gly, whose C-terminal carries an amide group and which has a molecular weight of 570.959: that this physiologically active substance can efficiently inhibit cancer cell growth and that the substance has efficient biological cell-control activity.

The biological cell-control agent, for instance, a cancer cell growth-control agent according to the present invention comprises the penta-peptide described above as an effective component. The physiologically active substance, as the effective component, according to the present invention has an amino acid sequence comprising 5 amino acid residues from the N-terminal: Asp-Ile-Leu-Arg-Gly and whose C-terminal carries an amide group (SEQ ID NO:5), as has been discussed above. As has also been described above, the effective component can be prepared by isolating and purifying or may be prepared according to any known method using any known peptide synthesis device.

The physiologically active substance of the present invention permits efficient reduction of, for instance, living cancer cells. More specifically, the substance ensures a certain change in the stage of the cancer cell cycle and permits the shift of the cancer cells to the temporary dormancy or resting state. The physiologically active substance having such a function can be effectively used as a cancer cell growth-control agent and accordingly, may practically be used as a carcinostatic agent. The substance would have such excellent effect that it can solve the problem of harmful effects on the normal cells (apoptosis) associated with the conventional anti-cancer agents or it does not adversely affect most of normal cells in the resting stage and it can inhibit only the proliferating cells. In addition, this physiologically active substance can serve as a biological cell-control factor (cell regulator) to thus reversibly control the cell growth. For instance, the substance can efficiently inhibit proliferation of cancer cells and is a low molecular weight penta-peptide comprising 5 amino acid residues and a novel substance in the biological world. Moreover, this physiologically active substance is completely different in the molecular structure from the known Cecropin and Pierisin and the substance can efficiently inhibit any growth of, for instance, rat hepatoma cells. In respect of the mechanism for inhibiting cancer cells, the substance can inhibit such cells according to a specific control mechanism, which has never been encountered in the conventional techniques. In other words, it is characterized in that it can modify the cell cycle and that it can reversibly control the cell growth. In addition, it is a physiologically active substance useful in the elucidation of the mechanism of the cell cycle.

In the case of proliferation of cancer cells, the stages of the cycle depend on the basic cell cycle like the usual cell proliferation as will be detailed below, but the cell growth continues to proceed due to the abnormality in its check point-control system. In this respect, the term "check point-control system" means a system for preventing any occurrence of catastrophic damage of the gene in the cell when any defect takes place in the cell cycle. The cell cycle can thus be controlled by making the most use of such a function. Contrary to such cell proliferation, any cell division never takes place in the G0 stage (resting stage) in the case of the cells after the completion of growth and differentiation. In general, the growing cell undergoes the following cell cycle stages. That is, the cell proceeds from a G0 stage (resting stage) to a G1 stage (DNA replication-determining stage) and then proceeds from a G2 stage (mitotic division-preparation stage) to an M stage (cell division stage) through an S stage (DNA replication stage) (in this specification, this is abbreviated "G2/M stage"). Thereafter, the cell again proceeds to the G0 stage or sometimes directly to the G1 stage (DNA replication-determining stage) without experiencing the G0 stage (in this specification, this is abbreviated "G0/G1" stage.

The physiologically active substance of the present invention is characterized in that it serves to inhibit any increase of the number of cancer cells and that it can substantially change the cycle stage of the living cancer cells. More specifically, the substance can serve to shorten the S stage corresponding to the DNA replication stage and to extend the G0 stage or the resting stage and the G1 stage corresponding to the DNA replication-determining stage. Thus, the physiologically active substance of the present invention efficiently inhibits any growth of the cancer cells. The physiologically active substance of the present invention derived from the *Antheraea yamamai* has a specific effect on the specific cancer cell cycle stage as has been discussed above and therefore, it is clear that the substance would efficiently inhibit any proliferation of the cancer cells.

As has been described above, the physiologically active substance of the present invention serves to maintain the dormancy of the pre-larvae of *Antheraea yamamai* over a long period of time as a physiologically active function. In general, it is recognized that the interruption of cell growth and the maintenance of a low energy condition characterize the dormancy of the organism. Therefore, the functions of this substance can be used in various fields and as an example, the substance can be used to control any proliferation of cancer cells of mammals. Moreover, it is expected that the substance can inhibit the cell growth of a large number of organisms and further can be used for the development of a long-term preservative effective in the level of cells or living body.

In general, if a protein has a high molecular weight, such a protein suffers from a serious problem in that it causes an antigen-antibody reaction upon practical application thereof to a living body. As has been described above, Cecropin derived from silkworm has a molecular weight of about 4 K and Pierisin derived from cabbage butterfly has a molecular weight of 98 K. Therefore, they are liable to cause an antigen-antibody reaction when administered to a living body. On the other hand, the physiologically active substance derived from the *Antheraea yamamai* according to the present invention is a penta-peptide having a low molecular weight on the order of 571.959 and thus has such characteristic properties that it never undergoes any antigen-antibody reaction even when administered to organisms other than insects. The peptide prepared by isolating and purifying it from an insect or the like or the peptide artificially synthesized may effectively show its effect. For this reason, this peptide having such a specific function as carcinostatic activity can directly be administered to a variety of animals without any preliminary modification. A low molecular weight peptide such as the peptide of the present invention never acts as an antigen in the higher animals and thus the peptide can show its carcinostatic function when externally administered to a living body. This is because, even if a low molecular weight oligopeptide externally invades a living body, it never serves as an antigen in the antigen-antibody reaction of the immunoglobulin of the vertebrate. Moreover, the present invention also permits easy studies of and inspection for possible functions by external administration of a synthetic peptide to a living body.

Moreover, the peptide of the present invention never causes any antigen-antibody reaction as has been described above and possesses a cell growth-control effect and therefore, it is quite promising as a leading compound for the development of a novel medicine or a carcinostatic agent. In addition, the peptide serves to continuously prevent any increase of the number of living cancer cells and can make the cycle stage of the cancer cells change to thus temporarily interrupt any cell proliferation. The peptide of the present invention is different, in the mechanism of action, from any conventional carcinostatic agent in this respect. In other words, it has in general been said that the G0 stage and the G1 stage in the cell cycle require the longest period of time. The physiologically active substance of the present invention serves to shorten the S stage corresponding to the DNA replication stage and to extend the G0 stage or resting stage and the G1 stage corresponding to the first stage. Thus, the physiologically active substance of the present invention, which serves to extend these two stages, is fundamentally different from the conventionally reported substances showing cancer cell-inhibitory effect and derived from insects and can efficiently inhibit any proliferation of cancer cells. On the other hand, either Cecropin or Pierisin serves to induce condensation and/or fragmentation of nuclei accompanied by the apoptosis to thus reduce the number of viable cells. Contrary to this, the physiologically active substance of the present invention serves to extend the G0 and G1 stages in the cell cycle, while shortening the S stage to thus extend the cell cycle of the living cells and to ultimately inhibit any cell proliferation. Therefore, the physiologically active substance of the present invention does not induce death of cells in the growth of cancer cells, but serves to control the cell cycle and to in turn inhibit the cell growth and to thus prevent any increase in the number of cells.

The foregoing physiologically active substance may likewise be isolated from wild *Antheraea yamamai* in the stages other than the pre-larval dormancy stage or from insects other than the *Antheraea yamamai*, for instance, which have dormancy at the same stage or the insects at other stages. The substance may be isolated from other wild silkworms such as *Antheraea pernyi* or camphor silk moth (*Dictyoploca japonica* Butler). This is because insect's hormones show different functions depending on the kinds of insects and the stages thereof even if the structures thereof are identical to one another. More specifically, insects are, in respect of the dormancy, classified into those falling into embryonic dormancy such as "KAIKO" (domestic silkworm); those falling into larval dormancy such as cabbage army worm; those falling into pupal diapause such as "SAKUSAN" (camphor silk moth) and cabbage butterfly; and those falling into adult diapause such as lady beetles and bird lice, in addition to those falling into pre-larval dormancy such as *Antheraea yamamai*. It can of course be predicted that the physiologically active substance of the present invention can be isolated from insects in all kinds of dormancy. Therefore, the same penta-peptide and related substances can be identified from a variety of insects as cell regulators such as cancer cell growth-inhibitory factor. The penta-peptide can be extracted from the whole body of such a wide variety of insects according to the procedures shown in FIG. 1 as has been described above.

The penta-peptide, which can serve to control any proliferation of cancer cells is a novel peptide possessing an anticancer function since there has never been found any known peptide even in the computer search (BLAST and FASTA).

It has also been demonstrated that the foregoing physiologically active substance derived from *Antheraea yamamai* is one having a biological cell-control function such as a cancer cell proliferation-inhibitory function in addition to the foregoing dormancy-maintaining function. This substance is, in itself, useful as a biological cell-control agent and, in future, will become important as a leading compound for the development of a novel medicine including an agent for treating cancer.

As has been discussed above, a physiologically active substance, which has endocrinologically never been known in the field of the insect and which is a biological cell-control factor, has been revealed, for the first time, by the present invention.

The low molecular weight peptide having gene Any-RF according to the present invention can efficiently inhibit the proliferation of cancer cells without being accompanied by any side effect and can inhibit the proliferation of rat hepatoma cells. Therefore, it would be highly probable that the peptide may effectively inhibit the proliferation of cancer cells such as human hepatoma cells, liver cancer cells, lung cancer cells, gastric carcinoma cells, breast cancer cells and hysterocarcinoma cells and thus may efficiently control biological cells.

The cell-control agent of the present invention may be formed into a variety of pharmaceutical preparations, like the usual drugs, and may have a variety of dosage forms, for instance, solid medicines such as tablets, sugar-coated tablets, hard capsules, or soft capsules; and liquid preparations such as solutions, emulsions or suspensions, for oral administration. Moreover, these pharmaceutical preparations can be prepared using various kinds of well-known additives such as vehicles, stabilizers, antiseptics, solubilizing agents, wetting agents, emulsifying agents, lubricants, sweetening agents, colorants, perfumes, buffering agents and antioxidants according to need. The effective amount of the cell-control agent of the present invention in general ranges from 50 to 350 mg/kg and preferably 100 to 200 mg/kg. The pharmaceutical preparation may be administered to a living body by any means insofar as the preparation can be administered to the interior of the living body and the preparation can be administered, for instance, orally, intravenously or intraperitoneally.

The foregoing peptide of the present invention as the physiologically active substance is almost free of an) side effect in the living body as compared with the conventional Cecropin and Pierisin and any acute toxicity is not observed at all. More specifically, the peptide of the present invention was administered to rats and mice through two routes, i.e., oral and percutaneous routes, in an amount of 0.5 g per unit body weight (1 kg) and the acute toxicity test was carried out according to the predetermined method. As a result, there was not observed any acute toxicity such as convulsion and vomiting in both of these animals. Moreover, the testis of the genital organ was removed from each animal after the acute toxicity test and the tissue was examined with a microscope. However, any abnormality was not observed at all. In addition, the peptide of the present invention is a low molecular weight penta-peptide and therefore, it never causes any antigen-antibody reaction and it is safe.

Incidentally, the base sequence coding for the peptide of the present invention or the amino acid sequence: Asp-Ile-Leu-Arg-Gly may be, for instance, 5'GAY-ATH-YTN-MGN-GGN-3'.

EXAMPLES

The present invention will hereunder be described in more detail with reference to the following Examples and Comparative Examples, but the present invention is by no means limited to these specific Examples. In the following Examples, the following various tests were carried out using a synthetic peptide w hose amino acid sequence was identical to that of the isolated peptide.

(1) Isolation of Active Fractions

The dormancy-control substance of the present invention was isolated and purified as follows according to the procedures as shown in FIG. 1.

The pre-larvae of *Antheraea yamamai* were picked out from eggs in the dormancy state and within one month from the oviposition, followed by immediate freezing thereof with liquid nitrogen and subsequent storage of them at $-80°$ C. till they were subsequently used. To about 1500 pre-larvae (about 6 g), there was added 10 volumes of an acid-methanol solution (methanol: water: acetic acid=90:9:1 (% by volume)), followed by trituration in a mortar and subsequent centrifugation at 10,000 g for 30 minutes to give a supernatant. These operations were repeated three times and then the combined supernatants were concentrated using a centrifugal vaporizer. Then the resulting concentrate was subjected to a heat-treatment at 100° C. for 10 minutes, followed by centrifugation at 10,000 g for 15 minutes. To the resulting supernatant, there was added cold acetone in such an amount that the final concentration of the supernatant was 80%, followed by centrifugation at 10,000 g for 15 minutes to give precipitates. The precipitates were dissolved in water and then introduced into an HPLC system. In this HPLC system, the aqueous solution was first passed through a Millipore Filter (SLLH R04 NL, 0.5 $\mu$m) available from Millipore Company, then eluted twice from a reverse phase high performance liquid chromatography column and finally eluted from a mixing-separation mode high performance liquid chromatography column to thus give an isolated and purified product.

In the first reverse phase high performance chromatography (RP-HPLC) step of this isolation method, the column used was TSKgel ODS-80Ts (available from Tosoh Corporation) and the same column was also used in the second RP-HPLC system. In the third mixing-separation mode high performance liquid chromatography, which comprised reverse phase and ion-exchange modes, the column used was RSpak NN-614 (available from Showa Denko K.K.). In either of these systems, acetonitrile was added to a 0.1% trifluoroacetic acid (TFA) aqueous solution (% by volume) to thus change the concentration (%) of acetonitrile. Thus, the active fractions were eluted from the column by making use of such a concentration gradient. The absorbance of each fraction was determined at 220 nm and the flow rate was set at 1 ml/min or 0.5 ml/min.

(2) Bioassay

In general, the activity of a repressive factor is determined using a non-dormancy type insect and evaluated on the basis of the rate of dormancy induction, but there is not any non-dormancy type strain in *Antheraea yamamai*. For this reason, the pre-larva falling into dormancy was treated with an imidazole compound KK-42 to thus awake from the dormancy (Suzuki et al., Int. Society for Wild Silkmoth, 1989, pp. 79–84; Suzuki et al., J. Insect Physiol., 1990, pp. 855–860, the disclosure of which is hereby incorporated by reference herein), the active fraction was injected into the pre-larva after 24 hours from the awakening and the dormancy-control function of the fraction was evaluated on the basis of an increase in the average days required for awakening from the dormancy and the reduction in the rate of the awakening from the dormancy.

(3) Determination of N-Terminal Amino Acid Sequence

The N-terminal amino acid sequence was determined using Protein Sequencer. The N-terminal amino acid sequence of the dormancy-control substance isolated and purified was analyzed using Peptide Sequencer G1000A (available from Hewlett Packard Company).

(4) Mass Spectrometric Analysis

Using MALDI-TOF MS (Matrix-Assisted Laser Desorption Ionization-Time-of-Flight mass spectrometer)(available from Voyager PerSeptive Biosystems Company), the substance isolated and purified and a sample peptide having an amino acid sequence identical to that of the substance and prepared by a known method (0.5 $\mu$l each) were injected into sample plate holes of the mass spectrometer and they were mixed with the same volume of a matrix, which was prepared by mixing a 0.1% trifluoroacetic acid (TFA) aqueous solution and acetonitrile in a ratio of 50:50 (% by volume) and then saturating the resulting mixture with $\alpha$-cyano-4-hydroxy cinnamic acid ($\alpha$-CHCA). After drying, the molecular mass was determined in terms of the matrix converted into a positive ion.

(5) Synthesis of Peptide

A peptide whose primary structure was completely identical to that of the peptide isolated and purified by the foregoing procedures according to the present invention was prepared by the following method. More specifically, peptides Asp-Ile-Leu-Arg-Gly-NH$_2$ (SEQ ID NO:5, the peptide of SEQ ID NO:1 having the C-terminal amidated) (abbreviated as DILRG—NH$_2$ or RF—NH$_2$) and Asp-Ile-Leu-Arg-Gly-COOH (SEQ ID NO:1) (abbreviated as DILRG—COOH or RF—COOH) were prepared according to the usual procedures using a peptide synthesizer (PSSM-8 available from Shimadzu Corporation). The purification of these peptides were carried out using a reverse phase column ULTRON VX-ODS (20 mm×250 mm, available from Shinwa Kako K.K.) connected to an HPLC system (LC-10A, available from Shimadzu Corporation). The elution was carried out at a flow rate of 8 ml/min and using an acetonitrile concentration gradient (1 to 5% for 0 to 5 minutes; 5 to 60% for 5 to 35 minutes) in the presence of a 0.1% TFA to thus give active fractions. The absorbance at 220 nm was monitored. The purified peptide was mixed with an equivalent amount of a matrix (50% acetonitril/0.1% TFA saturated with $\alpha$-CHCA) on the sample plate, followed by drying and confirmation of the purity thereof using MALDI-TOF MS (available from Voyager PerSeptive Biosystems Company).

Two kinds of peptides DILRG—NH$_2$ (SEQ ID NO:5, the peptide of SEQ ID NO:1 having the C-terminal amidated) (purity: not less than 95%, determined using HPLC and TOF-MS) and DILRG—COOH (SEQ ID NO:1) (purity: not less than 95%, determined using HPLC and TOF-MS) were synthesized according to the foregoing method and they were used in the following Examples.

(6) Cells and Composition of Culture Medium

Rat hepatoma cells (dRLh 84) were used and these cells were cultivated in Dulbecco's modified Eagle medium (DMEM) containing 4 mM glutamine, 50U/ml penicillin, 100 $\mu$g/ml kanamycin, and supplemented with 10% neonatal calf serum. In respect of the foregoing cells, the cultivation thereof was carried out at 37° C. in a wet atmosphere including 5% $CO_2$.

(7) Assay for Cancer Cell Growth-Control

The used culture medium was removed from a (100 mm dish (generally schale) in which cells were cultured and the dish was once washed with PBS(−) (prepared by removing Ca and Mg ions from phosphate buffered saline). To the dish, there was gently added 1.5 ml of a 10% trypsin solution so that the solution uniformly spreaded throughout the dish, 1 ml of the solution was removed, the dish was maintained at 37° C. for 5 minutes and it was confirmed with a microscope that the cells were pealed off from the bottom of the dish. Then 9.5 ml of a fresh DEME medium was added to the dish and the cells were separated into individual cells by pipetting to thus suspend the cells in the medium. Dishes of Φ100 mm were inoculated with this suspension in a dilution of ⅟₂₀ (total amount: 10 ml), followed by introduction thereof into an incubator and cultivation for 24 hours. Each peptide was added to these dishes in a predetermined concentration, followed by cultivation at 37° C., determination of the number of cells using a blood counting plate after 24 and 48 hours from the initiation of the cultivation to thus inspect the peptides for their cell growth-control functions.

(8) Morphological Observation

After recovering the cells treated with each peptide by centrifugation. 100 µl of ½ PBS(−) was added to the cells to give a suspension. Then two drops of a Carnoy's fixative was added and suspended and then 1 ml of a Carnoy's fixative was overlaid thereon. This overlay solution was gently stirred, followed by allowing to stand for 5 minutes at room temperature, centrifugation (at 4000 rpm for 5 minutes), removal of the supernatant and addition of a small amount of Carnoy's fixative to thus give a suspension. A drop of this suspension was placed on a slide glass plate and then air-dried. In addition, a drop of the fixative was dropwise added to the cells and again air-dried. Giemsa staining liquid was overlaid onto the air-dried cells to thus stain the cells at room temperature for 30 minutes, followed by water washing, air-drying and sealing. Then any change of the nuclei was examined with a microscope.

(9) Flow Cytometric Analysis (FACS)

The cells treated with each peptide was fixed at 4° C. for 4 hours using 70% ethanol. The fixed cells were washed with PBS(−), then treated with 2 mg/ml of RNaseA at 37° C. for 30 minutes to thus analyze the RNA. Thereafter, the cells were stained with propidium iodide (25 µg/ml) for not less than 30 minutes and filtered through a nylon mesh. Then the intensity of fluorescence (DNA content per cell) observed for 10,000 cells was analyzed using a flow cytometer (FACSVANTAGE available from Becton Dickinson Company).

Example 1

Isolation of Active Fraction

Figure 2:
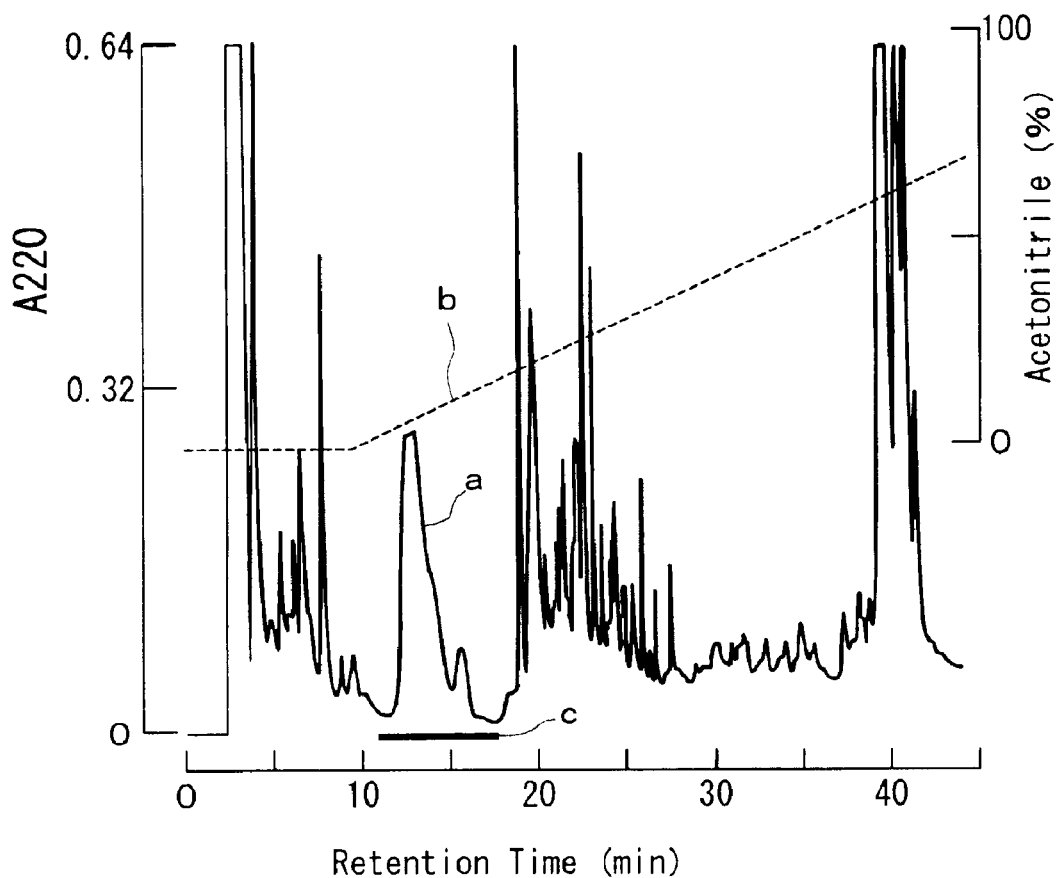
FIG. 2 is a spectrum showing the elution peaks of active fractions, obtained by a first HPLC system (reverse phase HPLC) in the process for isolation of the dormancy-control substance according to the present invention.
Figure 3:
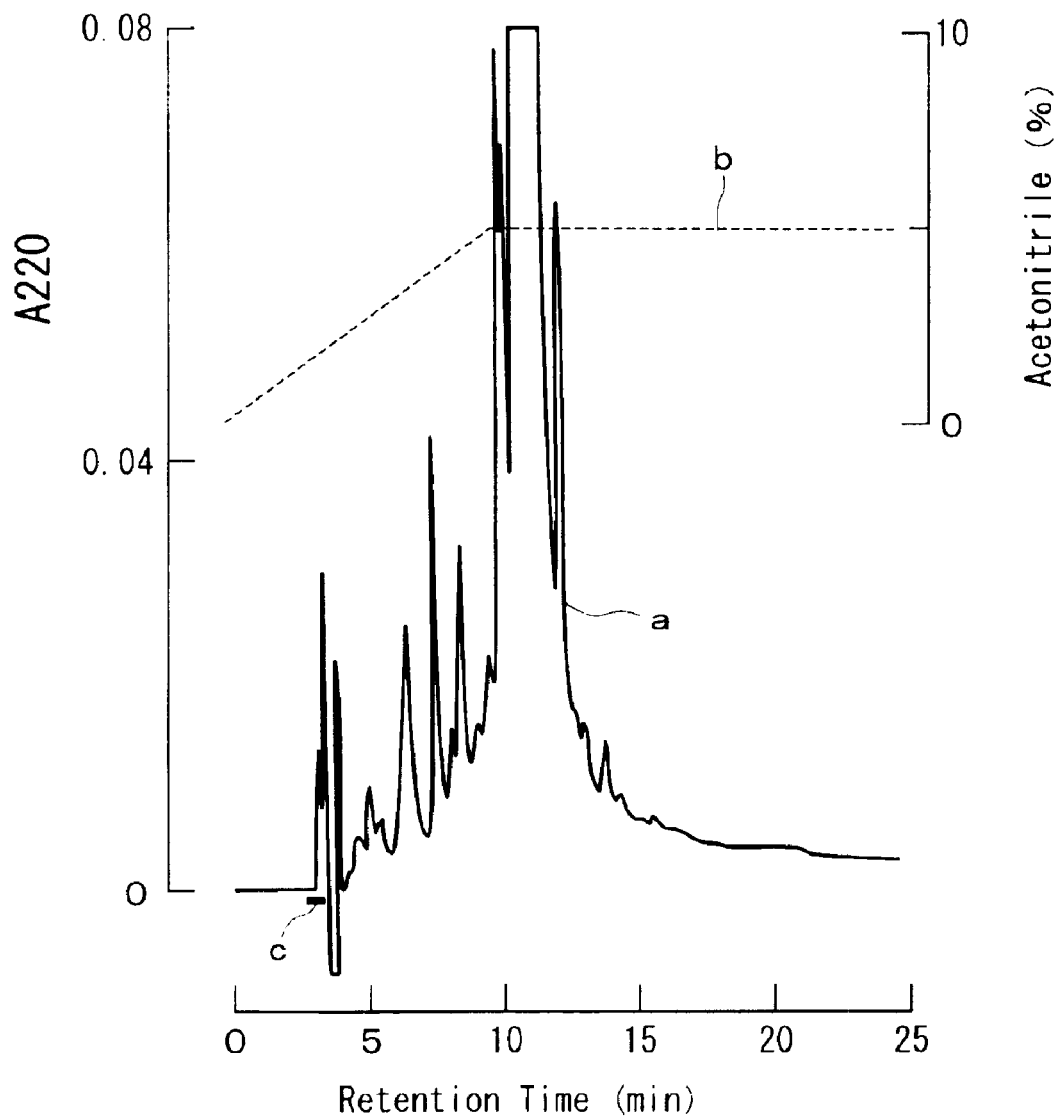
FIG. 3 is a spectrum showing the elution peaks of active fractions, obtained by a second HPLC system (reverse phase HPLC) in the process for isolation of the dormancy-control substance according to the present invention.
Figure 4:
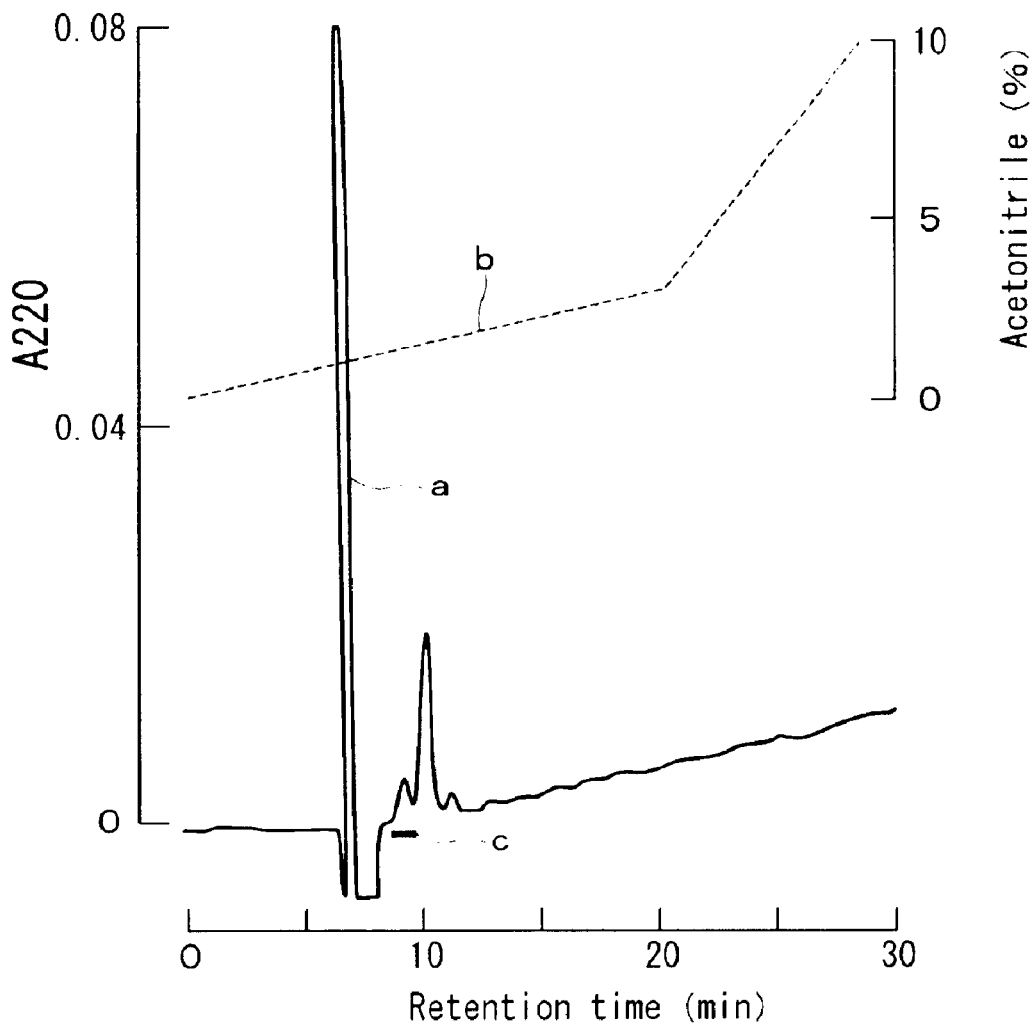
FIG. 4 is a spectrum showing the elution peaks of active fractions, obtained by a third HPLC system (mixing-separating mode) in the process for isolation of the dormancy-control substance according to the present invention.

To isolate and purify a dormancy-control substance from about 1,500 pre-larvae of *Antheraea yamamai*, there were used the processes described in detail in the foregoing section entitled "I) Isolation of Active Fraction". In the first RP-HPLC system, the active fractions were eluted within the elution time ranging from 11 to 17 minutes (FIG. 2). In the second RP-HPLC system in which the active fractions were injected, the desired activity was observed for the initial peak eluted after about 3 minutes from the initiation of the elution (FIG. 3). In the subsequent third mixing-separation mode HPLC system in which the active fraction obtained in the second RP-HPLC system was injected, the desired activity was observed for the peak eluted after about 9.5 minutes from the initiation of the elution (FIG. 4). We assumed that the isolation and purification were completed by a series of the foregoing operations and the final active fraction isolated from the 1,500 pre-larvae falling into dormancy was analyzed using a peptide sequencer (G1000A described above available from Hewlett Packard Company).

Example 2

Determination of Structure of Control Substance

Figure 5:
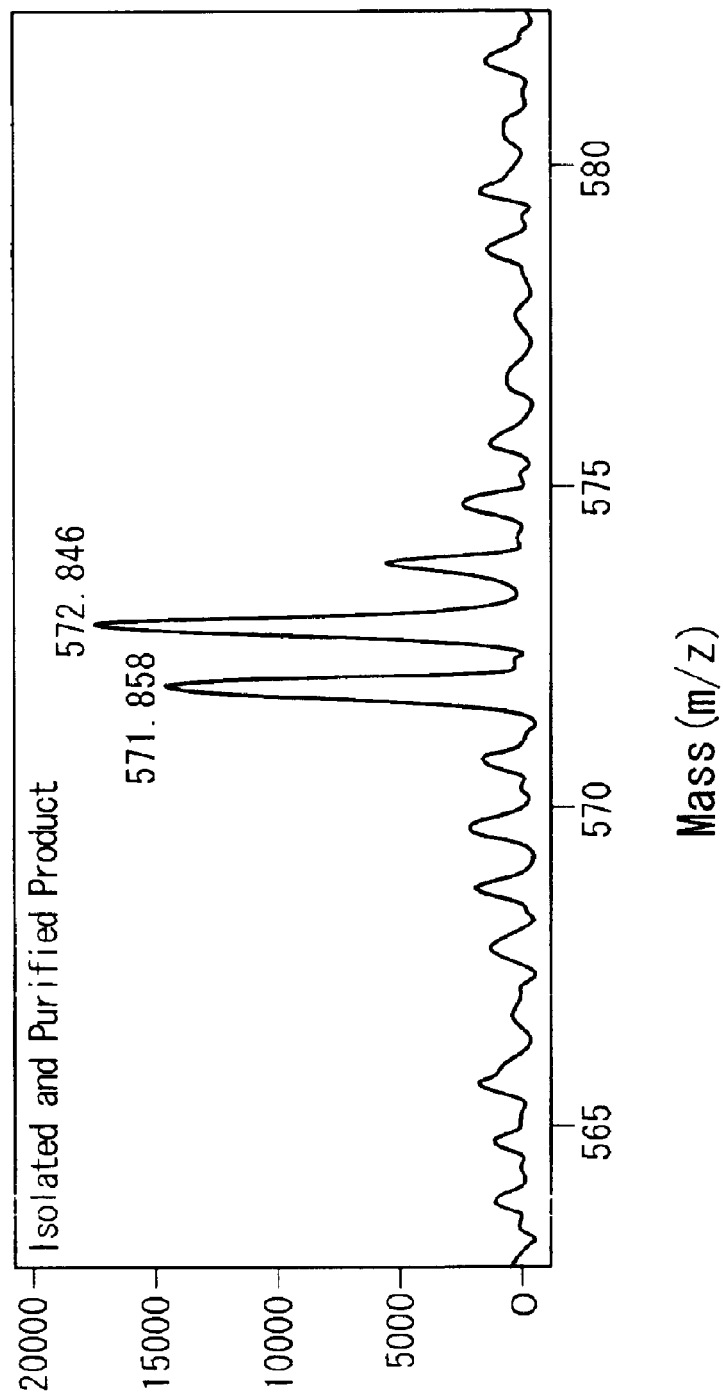
FIG. 5 is a mass spectrometric spectrum used for determining the molecular weight of a peptide as an isolation and purification product, which corresponds to the dormancy-control substance according to the present invention.
Figure 6:
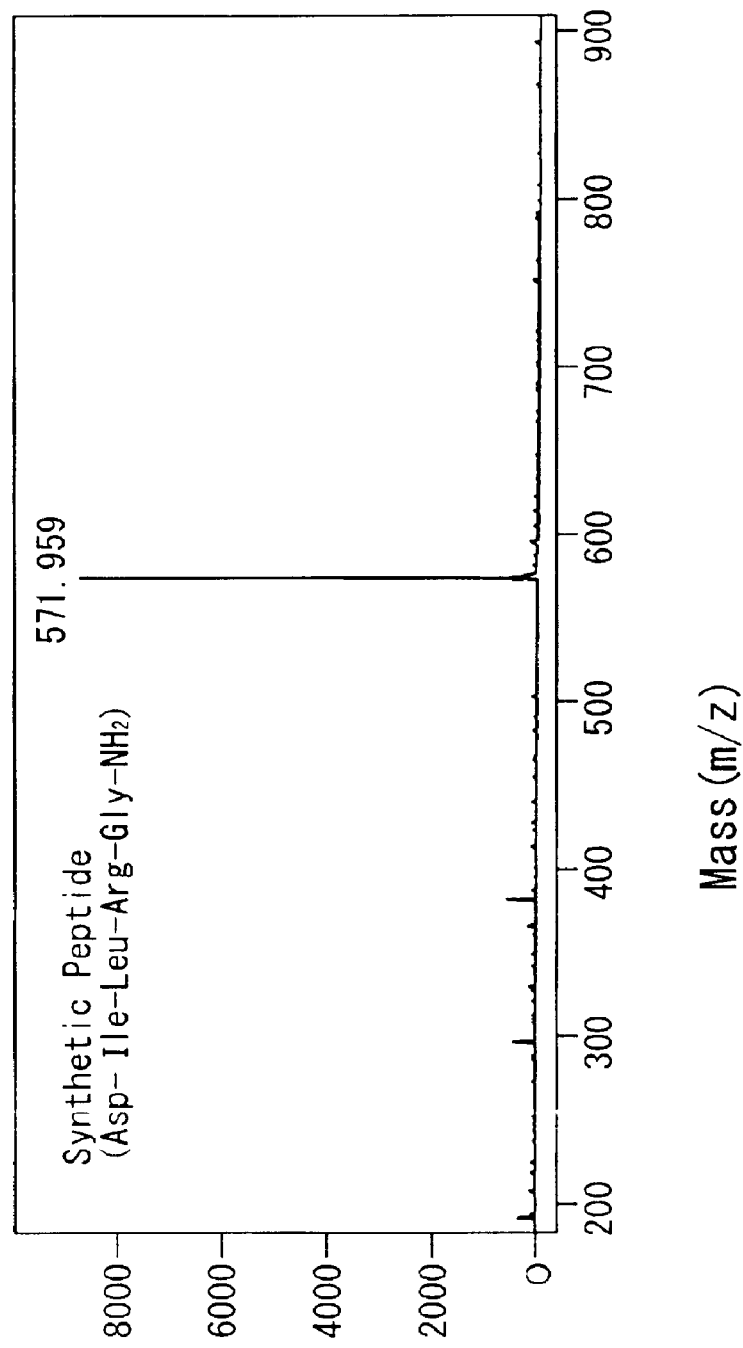
FIG. 6 is a mass spectrometric spectrum used for determining the molecular weight of a synthetic peptide (Asp-Ile-Leu-Arg-Gly-NH$_2$, SEQ ID NO:1 having the C-terminal amidated) having an amino acid sequence and C-terminal identical to those observed for the dormancy-control substance according to the present invention.
Figure 7:
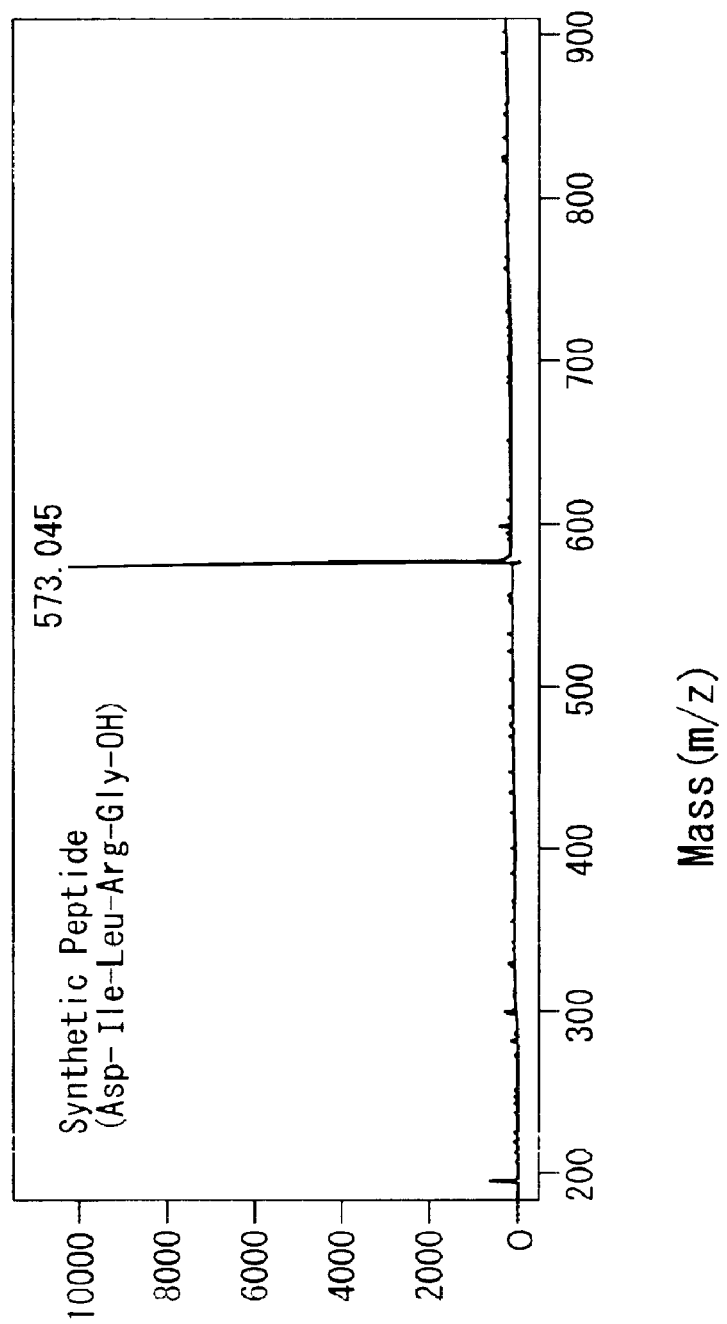
FIG. 7 is a mass spectrometric spectrum used for determining the molecular weight of a synthetic peptide (Asp-Ile-Leu-Arg-Gly-OH, SEQ ID NO:1) having an amino acid sequence identical to that of the dormancy-control substance according to the present invention and a C-terminal different from that of the latter.

After dissolving, in pure water, 100 µl of the dormancy-control substance prepared in Example 1, the sequencing was carried out up to 10 cycles from the N-terminal using an aqueous solution, which contained 25 µl of the dormancy-control substance. As a result, it was confirmed that the amino acid sequence of the active substance having a dormancy-control activity was Asp-Ile-Leu-Arg-Gly. To examine whether the C-terminal of the active substance was in an amidated form ($-NH_2$) or a free acid form ($-COOH$), this isolated and purified product and the foregoing two synthetic peptides were analyzed using MALDI-TOF MS (mass spectrometer). As a result, there were observed two large peaks at 571.858 and 572.846 for the isolated and purified product (FIG. 5), a maximum peak at 571.959 for the synthetic peptide: Asp-Ile-Leu-Arg-Gly-$NH_2$ (the peptide of SEQ ID NO:1 having the C-terminal amidated) (FIG. 6) and a maximum peak at 573.045 for the synthetic peptide: Asp-Ile-Leu-Arg-Gly-COOH (SEQ ID NO:1) (FIG. 7).

The results indicate that two types of amino acid sequences would be present in the living body. Therefore, the physiological activities of the isolated and purified product and the two synthetic peptides were investigated in the following Examples to make clear whether the true active peptide had the C-terminal in an amidated or free acid form.

Example 3

Bioassay of Isolated and Purified Product and Synthetic Peptides

The isolated and purified product and two kinds of the synthetic peptides having an amino acid sequence identical to that of the product and having C-terminals in the amidated form and free acid form respectively were injected into pre-larvae of *Antheraea yamamai*, which had been destined to awake from the dormancy by treating them with an imidazole compound KK-42 to thus examine the state of the larvae awakening from the dormancy and average days required till the larvae awoke from the dormancy and to evaluate the rate of larvae awaken from the dormancy. More specifically, 0.1 µg/0.5 µl each of a KK-42 solution in acetone was applied on the ventral portion of each larva to thus awake 100% of the larvae from the dormancy. Subsequent to the completion of the treatment for awakening from the dormancy, 0.05 µl each of distilled water was injected to each larva after 24 hours from the completion of the treatment and this group of larvae was used as the control group. In the case of the isolated and purified product, a solution whose concentration was adjusted in such a manner that 100 pmol of the product was present in 0.05 µl of distilled water was injected into each larva, while in the case of the synthetic peptides in the amidated and free acid forms, 100 pmol/0.05 µl each of the peptide was injected into each larva. In any case, the larvae were inspected for the number of larvae falling into dormancy, the number of larvae awakening from the dormancy, the number of died larvae and the average days required till awakening from the dormancy (diapause termination) to thus evaluate the rate of larvae awakening from the dormancy. The results thus obtained are shown in the following Table 1.

TABLE 1

Effect of Isolated and Purified Product and Synthetic Peptides on Awakening from Dormancy of Pre-larvae of *Antheraca yamamai*

| Injected Sample (injected amount) | N | Number of Insects | | | No. of Days[3] | Rate[4] |
|---|---|---|---|---|---|---|
| | | Dor[1] | Awa[2] | Died | | |
| Control Group (distilled water, 0.05 μl) | 10 × 3 | 0 | 30 | 0 | 5.79 ± 0.67 | 100 |
| Purified Peptide (isolated and purified product) Synthetic Peptides (100 pmol/0.05 μl) | 10 × 3 | 17 | 13 | 0 | 6.46 ± 0.80* | 43.3 |
| Asp-Ile-Leu-Arg-Gly-NH$_2$ | 10 × 3 | 14 | 16 | 0 | 6.72 ± 0.75** | 53.3 |
| Asp-Ile-Leu-Arg-Gly-COOH | 10 × 3 | 3 | 27 | 0 | 5.78 ± 0.77 | 90.0 |

Significance: *P < 0.03; **P < 0.002
[1]Dormancy; [2]Awakening from Dormancy; [3]Time (day) required till Awakening; [4]the rate of larvae awakening from dormancy.

As will be seen from the data listed in Table 1, the average days required till awakening from the dormancy and the rate of larvae awakening from dormancy observed for the control group were found to be 5.79 days and 100%, respectively. In respect of the isolated and purified product, the average days required till awakening as compared with the control group and the rate of larvae awakening from dormancy was reduced to 43.3%. In the case of the synthetic peptides, both of the average days required till awakening from the dormancy and the rate of larvae awakening from dormancy observed for the free acid type peptide are very close to the data for the control group, while those observed for the amidated type one are substantially close to those for the isolated and purified product. These data clearly demonstrate that the isolated and purified peptide possesses an amidated C-terminal and that this fact is a quite important factor for the physiological dormancy-maintaining function.

Consequently, the amino acid sequence of the repressive factor derived from *Antheraea yamamai* is Asp-Ile-Leu-Arg-Gly-NH$_2$ (SEQ ID NO:5, the peptide of SEQ ID NO:1 having the C-terminal amidated) and the molecular weight thereof can be determined by subtracting 1 (mass of a proton) from the measured value of the mass spectrometric peak or 570.959.

Example 4

Physiological Activity of Synthetic Peptides

There was synthesized a peptide having a structure identical to that of the peptide of the present invention, which had been subjected to structure determination (the peptide carrying an amidated C-terminal), as mentioned above, and the relation between the activity of the synthetic peptide and the concentration thereof was analyzed. In other words, if the pre-larvae falling into dormancy were subjected to a treatment for awaking them from the dormancy by applying them with an imidazole compound KK-42 (0.1 μg/0.5 μl) and then the synthetic peptide was injected to the pre-larvae thus treated, the number of larvae falling into dormancy, the number of larvae awakening from the dormancy and the number of died larvae were examined and the rate of larvae awakening from the dormancy was evaluated to confirm the degree of inhibition of awaking pre-larvae from the dormancy.

First, the imidazole compound KK-42 serving to awake pre-larvae from the dormancy was dissolved in acetone and 0.1 μg/0.5 μl each of the resulting solution was applied on the ventral portion of each pre-larva falling into dormancy. After 24 hours from the treatment with the KK-42 solution, 0.05 μl of distilled water was injected to the pre-larvae, followed by a second distilled water injection thereto after additional 24 hours and a third distilled water injection after additional 24 hours from the second distilled water injection (in the following Table 2, they are referred to as control 1, 2 and 3 respectively). And the rate of pre-larvae awaken from the dormancy (the rate of diapause termination) was evaluated in each case. In addition, 100 pmol/0.05 μl each of the synthetic peptide having an activity for maintaining the pre-larvae in the dormant state (activity for diapause maintenance) was injected into each pre-larva (it was injected once, twice and three times like the control and they are expressed in Table 2 in terms of x1, x2 and x3, respectively) to thus evaluate the rate of diapause termination for each group. The results thus obtained are summarized in the following Table 2.

TABLE 2

Influence of the mount of Synthetic Peptide on Diapause Termination of Pre-larva of *Antheraea yamamai*

| Sample Injected (Amount Injected × Injection Time) | N | Number of Insects | | | Rate[3] (%) |
|---|---|---|---|---|---|
| | | Dor[1] | Awa[2] | Died | |
| Control-1 (distilled water, 0.05 μl × 1)* | 10 × 3 | 0 | 30 | 0 | 100 |
| Control-2 (distilled water, 0.05 μl × 2)** | 10 × 3 | 1 | 29 | 0 | 96.7 |
| Control-3 (distilled water, 0.05 μl × 3)*** | 10 × 3 | 3 | 27 | 0 | 90 |
| Synthetic Peptides | | | | | |
| Asp-Ile-Leu-Arg-Gly-NH$_2$ (100 pmol/0.05 μl × 1) | 10 × 3 | 14 | 16 | 0 | 53.3 |
| Asp-Ile-Leu-Arg-Gly-NH$_2$ (100 pmol/0.05 μl × 2) | 10 × 3 | 21 | 9 | 0 | 30 |
| Asp-Ile-Leu-Arg-Gly-NH$_2$ (100 pmol/0.05 μl × 3) | 10 × 3 | 26 | 4 | 0 | 13.3 |

*The first injection was carried out after 24 hours from the treatment with KK-42.
**The second injection was carried out after 24 hours from the first injection.
***The third injection was carried out after 24 hours from the second injection.
[1]Dormancy; [2]Diapause Termination; [3]Rate of Diapause Termination.

As will be seen from the data listed in Table 2, the control-1, -2 and -3 show tendencies similar to one another while taking into consideration the population sizes of the pre-larvae falling into dormancy, the pre-larvae awaken from the dormancy and died pre-larvae as well as the rate of diapause termination. More specifically, almost all of the pre-larvae are in the diapause-terminated states irrespective of the number of distilled water injections. This clearly indicates that the injection of distilled water does not adversely affect the activity of KK-42 when the pre-larvae of Antheraea yamamai are destined to terminate diapause by the treatment with KK-42. In the case of the synthetic peptide, however, the rate of the diapause termination can be reduced from 53.3 to 30% in a comparison of the case in which the distilled water is injected once to the case in which it is injected twice and this can further be reduced to 13.3% by injecting the synthetic peptide three times. The foregoing specifically demonstrates the fact that the novel peptide whose structure is determined is a factor serving to maintain dormancy.

Example 5

Demonstration of Dormancy-Control Factor by Injection of Anti-Serum

A peptide: Cys-ε-Acp-Asp-Ile-Leu-Arg-Gly-$NH_2$ (SEQ ID NO:3) (CXDILRG-$NH_2$) was synthesized by adding an ε-Acp (aminocaproic acid) and cystine to the peptide of the present invention, KLH was used as a carrier protein to give a peptide—KLH conjugate. The conjugate, as an immunogen, was injected into domestic rabbit in Japan together with Freund's complete adjuvant to thus immunize the animal. The whole blood was collected from the animal after the elapse of the immunization period of two months, while monitoring the antibody-production by ELISA assay. The serum containing antibodies and produced above was used in experiments as an anti-serum. In this connection, the serum prepared from the blood collected prior to the injection and free of any antibody was used in control groups as a pre-serum.

Each of foregoing pre-serum and anti-serum was injected into pre-larvae of *Antheraea yamamai* falling into dormancy in an amount of 0.1 μl or 0.2 μl per insect. Thereafter, the population sizes of the pre-larvae falling into dormancy, the pre-larvae awaking from the dormancy and died pre-larvae were determined and the rate of diapause termination was thus evaluated. The results thus obtained are listed in the following Table 3.

TABLE 3

Effect of Anti-Serum on Diapause Termination of Pre-Larvae of *Antheraea yamamai*

| Sample Injected (Amount of sample injected) | N | Number of Insects | | | Rate[3] (%) |
|---|---|---|---|---|---|
| | | Dor[1] | Awa[2] | Died | |
| Pre-serum | | | | | |
| 0.1 μl | 10 × 3 | 30 | 0 | 0 | 0 |
| 0.2 μl | 10 × 3 | 30 | 0 | 0 | 0 |
| Anti-serum | | | | | |
| 0.1 μl | 10 × 3 | 27 | 3 | 0 | 10.0 |
| 0.2 μl | 10 × 3 | 19 | 11 | 0 | 36.7 |

[1]Dormancy; [2]Diapause Termination; [3]Rate of Diapause Termination.

Figure 8:
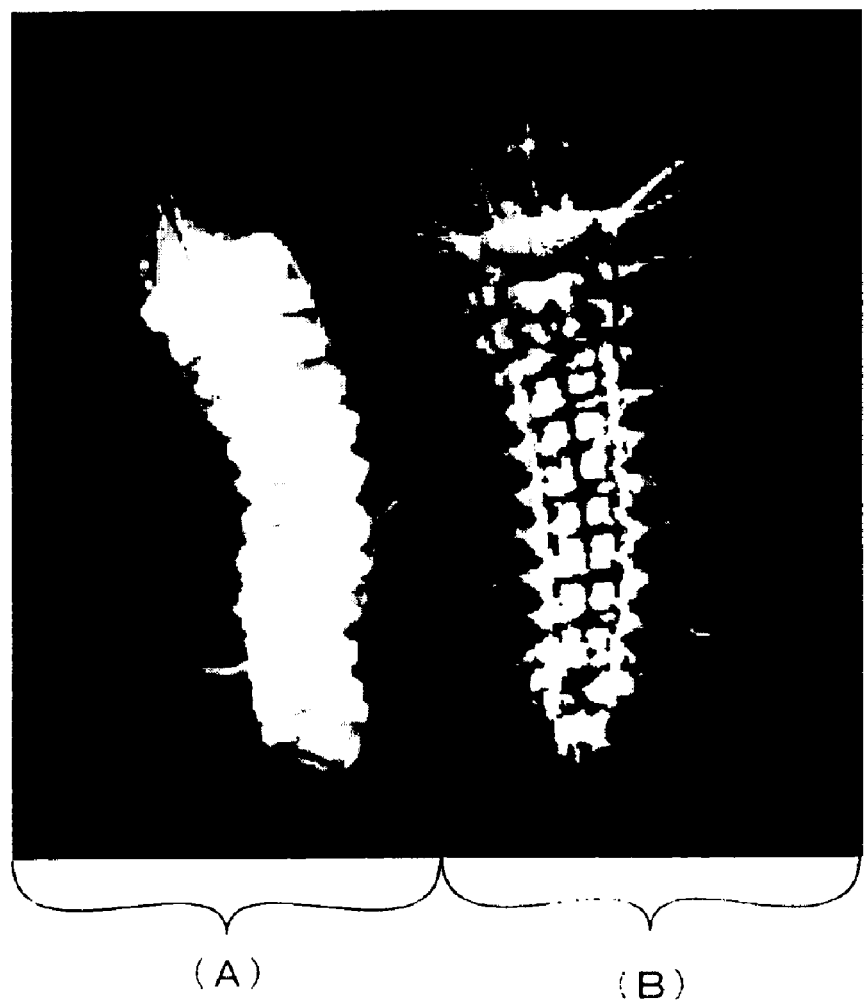
FIG. 8(A) is a photograph showing a pre-larva of Antheraea yamamai in which pro-serum is injected and in the dormancy state and FIG. 8(B) is a photograph showing a pre-larva of the silkworm in which anti-serum is injected and in the awakening state.

As will be seen from the data shown in Table 3, when pre-serum was injected in the control group, there was not observed any pre-larva awaken from the dormancy at the dose of both 0.1 μl and 0.2 μl or all of the pre-larvae maintained their dormancy state. However, when the anti-serum was injected, 10% and about 37% of the pre-larvae were awaken from the dormancy for the injection doses of 0.1 μl and 0.2 μl, respectively and the rate of diapause termination increased as the amount of the anti-serum injected increased. These results clearly demonstrate that the peptide of the present invention is a substance capable of controlling the dormancy in the living body. FIG. 8(A) is a photograph showing the sustained dormancy state of the pre-larva in which 0.2 μl of the pre-serum is injected and FIG. 8(B) is a photograph showing the diapause termination state of the pre-larva in which 0.2 μl of the anti-serum is injected. The results shown in Table 3 and FIGS. 8(A) and 8(B) clearly indicate that the peptide of the present invention whose structure is determined is a factor, which serves to control the dormancy state in the pre-larvae of *Antheraea yamamai*.

Example 6

Growth-Inhibitory Effect of Penta-Peptide on Rat Hepatoma Cells (dRLh84)

The inhibitory effect of the penta-peptide on the growth of cancer cells was examined as follows. As the cancer cells, there were used rat hepatoma cells (dRLh84), which were relatively easily available and whose cultivation was easy. To make clear the relation between the physiologically active substance (RF—$NH_2$) of the present invention and the growth of cancer cells, cancer cells were cultured in a cell culture medium supplemented with PBS(−) for a control group and culture mediums supplemented with 200 μg/ml each of the peptide whose C-terminal was amidated, i.e., RF—$NH_2$ and the peptide whose C-terminal was in a free acid form, i.e., RF—COOH, respectively, for the experimental groups. The number of cultured cells was adjusted to 3 to $5 \times 10^5$, and the cells were cultured with or without a predetermined amount of each peptide in the presence of 5% $CO_2$ at 37° C. Any morphological change in the cancer cells was directly examined with an inverted microscope using the culture mediums collected after 24 and 48 hours from the initiation of the cultivation. The resulting micrographs are shown in FIG. 9.

Figure 9:
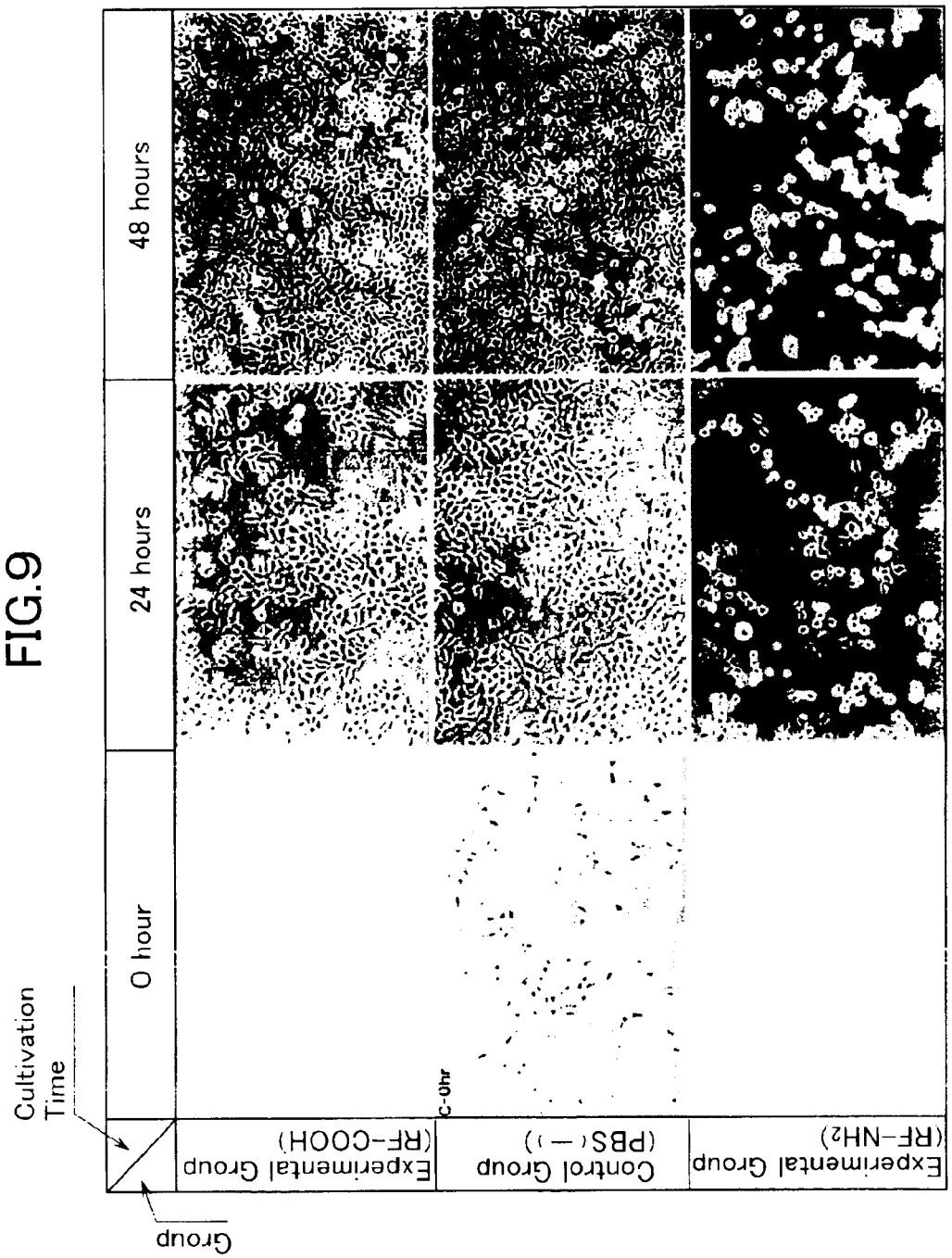
FIG. 9 is a micrograph showing the morphological change and growth inhibition observed for rat hepatoma cells (dRLh84) when using DILRG—$NH_2$ (SEQ ID NO:5, the peptide of SEQ ID NO:1 having the C-terminal amidated) or DILRG—COOH (SEQ ID NO:1).

As will be clear from the results shown in FIG. 9, the number of cancer cells was not increased at all after 24 and 48 hours in the experimental group in which RF—$NH_2$ was added as compared with the number of cells observed at the initiation of the cultivation (0 hour) and the shape of the cells was changed from a spindle-like shape to a circular shape (after 48 hours). Such a morphological change in the cell means that the cell state is changed from active division state to division-termination state. On the other hand, in the control group and the experimental group in which RF—COOH is added, the number of cells is quite conspicuously increased after 24 and 48 hours as compared with the number of cells observed at the initiation of the cultivation. The results shown in FIG. 9 indicate that the growth of the rat cancer cells is morphologically inhibited by the addition of the physiologically active substance of the present invention to the culture medium.

Example 7

Influence of Penta-Peptide Concentration on Rat Hepatoma Cell (dRLh84) Growth-Inhibitory Effect Rat hepatoma cells (dRLh84, $3 \times 10^5$ cells) were cultured in a culture medium, to which the peptide (DILRG—$NH_2$, SEQ ID NO:5, the peptide of SEQ ID NO:1 having the C-terminal amidated or DILRG—COOH, SEQ ID NO:1) was added in a predetermined amount (0, 50, 100, 150, 200 μg/ml) in the presence of 5% $CO_2$ at 37° C. for 40 hours. Thereafter, the culture medium was treated with trypan blue to determine the variable cell count. The results thus obtained are shown in FIG. 10.

Figure 10:
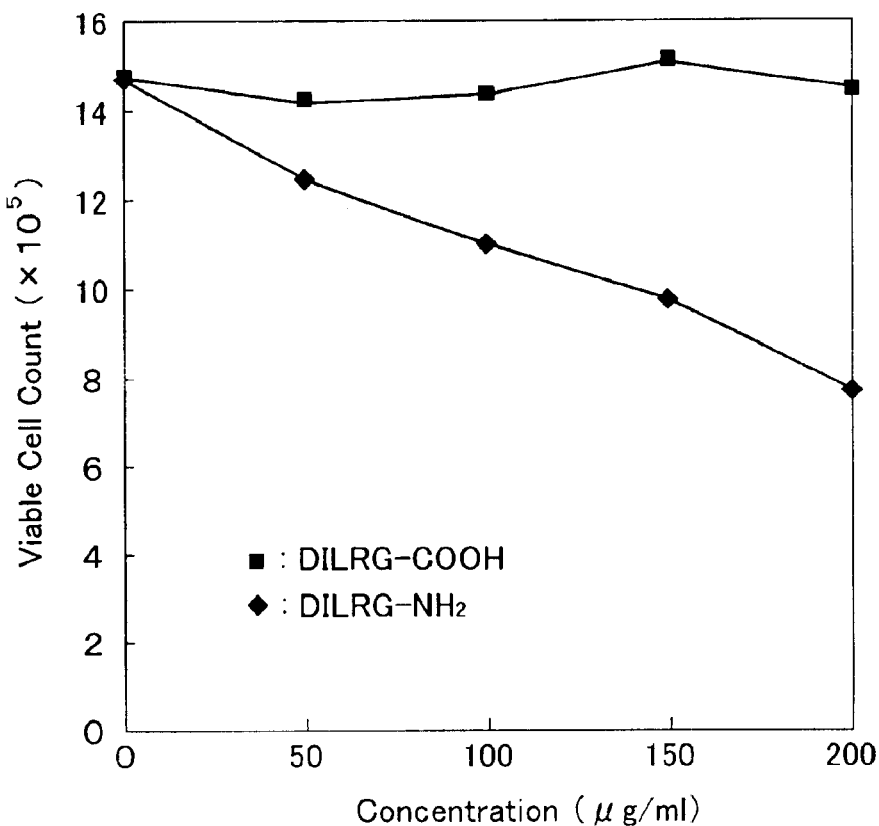
FIG. 10 is a graph showing the growth-control effect of DILRG—$NH_2$ (SEQ ID NO:5, the peptide of SEQ ID NO:1 having the C-terminal amidated) or DILRG—COOH (SEQ ID NO:1) on the rat hepatoma cells (dRLh84) in terms of the relation between the concentration and the viable cell count.

As will be seen from the results shown in FIG. 10, the viable cell count is on the order of $14.6 \times 10^5$ even at a high concentration of 200 μg/ml in the case of the experimental group in which RF—COOH is used and there is not any change in the cell proliferation activity. In the experimental group in which RF—NH$_2$ is added, however, the viable cell count is markedly reduced at a concentration of 50 μg/ml and it is reduced, at a high concentration of 200 μg/ml, even to a level of 7.7×10$^5$ cells, which corresponds to a half of that observed for the control group. The results shown in FIG. 10 indicate that the cancer cell growth-inhibition by the RF—NH$_2$ morphologically observed in Example 6 is in agreement with the reduction of the viable cell count. In addition, it has been found that the physiologically active substance of the present invention or the peptide whose C-terminal carries an amide group possesses a marked cancer cell growth-inhibitory effect, but the peptide whose C-terminal is in a free acid form never shows any such inhibitory effect.

Example 8

Relation between Proliferation Ability of Rat Hepatoma Cell (dRLh84) and Cultivation Time The results obtained in Examples 6 and 7 clearly demonstrate that the physiologically active substance derived from insects can inhibit the rat hepatoma cell growth. Thus, the cultivation time was extended to investigate the relation between the proliferation ability of cancer cells and the cultivation time using the physiologically active substance of the present invention. The method for cultivation used herein was identical to that used in Example 7. The cultivation time was extended up to 72 hours. The cultivation of 3×10$^5$ cells was carried out using a culture medium supplemented with PBS(-) for a control group and a cell culture medium for an experimental group, to which 200 μg/ml of the peptide (DILRG—NH$_2$) was added, in the presence of 5% CO$_2$ at 37° C. for 24, 48 and 72 hours, respectively. Thereafter, the culture medium was treated with trypan blue to determine the viable cell count. The results thus obtained are shown in FIG. 11.

Figure 11:
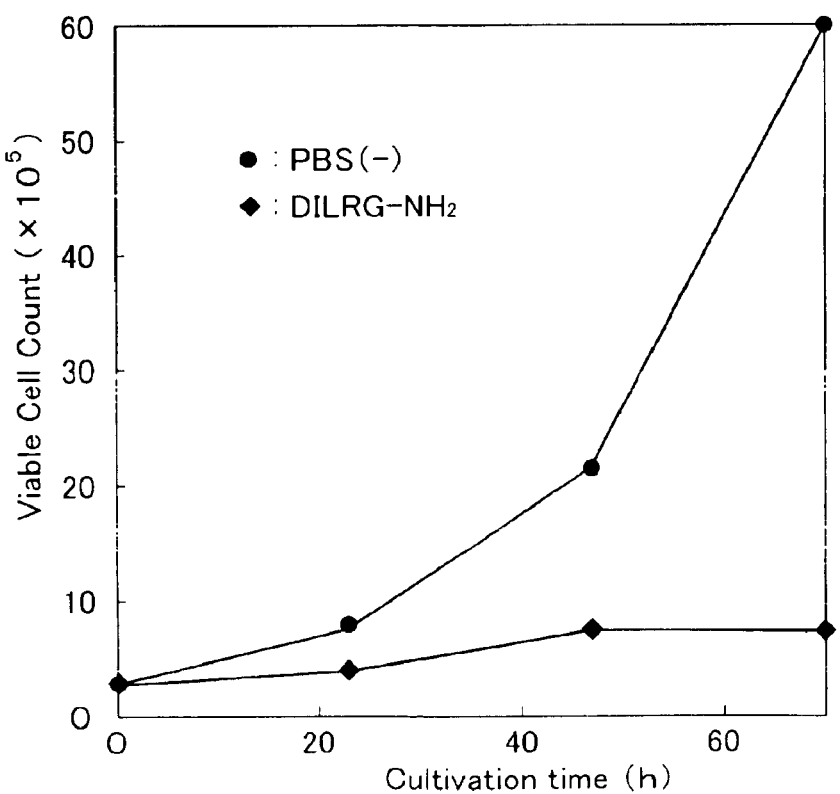
FIG. 11 is a graph showing the growth-control effect of DILRG—$NH_2$ (SEQ ID NO:5, the peptide of SEQ ID NO:1 having the C-terminal amidated) or PBS(−) on the rat hepatoma cells (dRLh84) in terms of the relation between the cultivation time and the viable cell count.

As will be seen from FIG. 11 the number of cells rapidly increases up to the cultivation time of 72 hours as the cultivation time increases in the case of the control group, or the viable cell count increases from 3×10$^5$ cells to 60×10$^5$ cells, (i.e. it increases by a factor of not less than 20). On the other hand, the number of cells increases from 3×10$^5$ cells to 8×10$^5$ cells within 72 hours in the case of the experimental group or it increases by a factor of only 2.7. This result indicates that the physiologically active substance of the present invention can reduce the cancer cell growth ability to a level of 1/7.5 time. In other words, it is clear that the physiologically active substance of the present invention shows an effect of inhibiting the cancer cell growth ability to a considerable level.

Then only the cultured cells were removed from the culture medium supplemented with the foregoing peptide after the cultivation for 48 hours and transferred to a fresh culture medium, and cultured under the same conditions used above to thus investigate any subsequent change in the cancer cell growth. As a result, the cancer cells whose growth had been once inhibited rapidly began to proliferate like the control group in which PBS(-) was added to the culture medium. Accordingly, this fact suggests that the continual presence of the peptide of the present invention is indispensable to the cancer cell growth inhibition and that the peptide can reversibly control the cell growth of all of the organisms.

Example 9

Analysis of any Change in Cell Cycle by Addition of Peptide

Figure 12A:
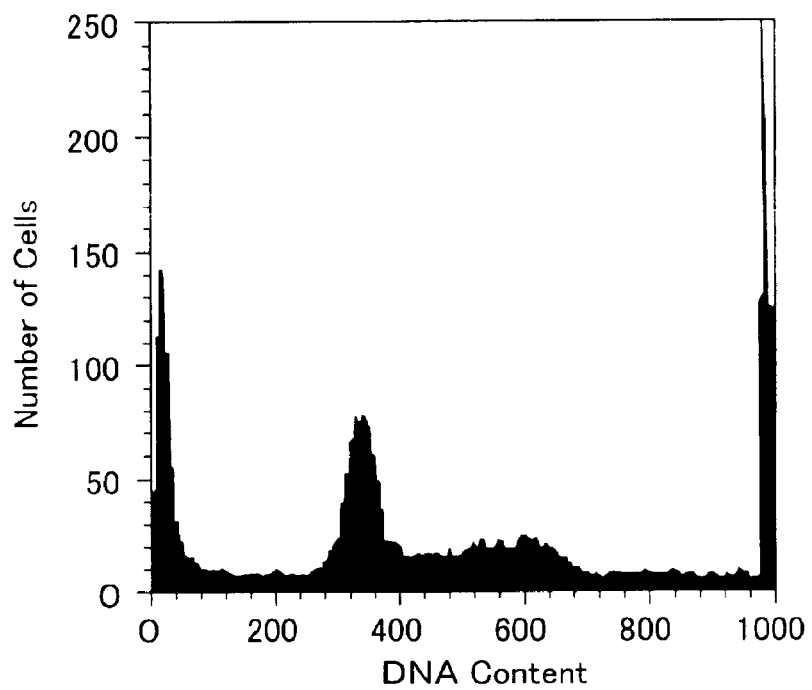
FIG. 12(A) is a spectrum (control group) showing the change of the cell cycle in the rat hepatoma cells (dRLh84) observed when PBS (−) is added.
Figure 12B:
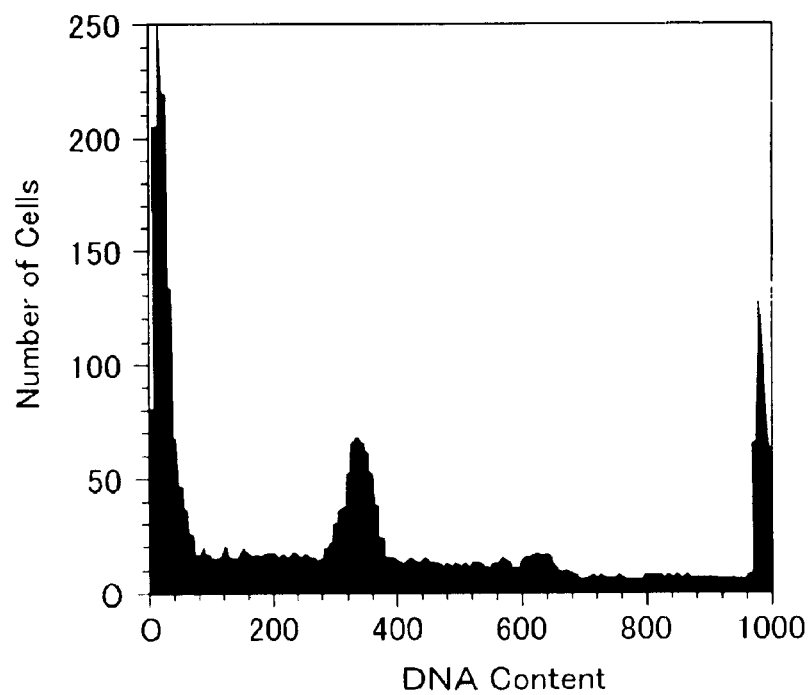
FIG. 12(B) is a spectrum (experiment group) showing the change of the cell cycle in the rat hepatoma cells (dRLh84) observed when RF—$NH_2$ is added.

The fact that the physiologically active substance of the present invention can inhibit the cell growth ability of the rat hepatoma is substantiated experimentally by the results obtained in Examples 6, 7 and 8 (FIGS. 9, 10 and 11). Thus, we tried to elucidate the mechanism of the inhibition. The peptide (DILRG—NH$_2$)(200 μg/ml) was added to the culture medium under the same conditions used in Example 6 and the cells were cultured, followed by fixing the cells after cultivation of 48 hours with ethanol and then staining the cells with propidium iodide. In addition, the same procedures used above were repeated using a culture medium supplemented with PBS(-) as a control group. The DNA content in the cells was analyzed using a flow cytometer. The results thus obtained are shown in FIGS. 12(A) and 12(B). The flow cytometric analysis employed for this purpose comprises the step of staining cells with propidium iodide, which is a fluorescent dye capable of being linked with DNA to thus determine the DNA content of the cell and this method permits the analysis of the cell cycle control. More specifically, the biological cell multiplies by cell division while undergoing the following cycle change: G0/G 1. S (DNA replication stage) and M stage (cell division stage) in this order. FIGS. 12(A) and 12(B) are graphs each showing the results obtained by determining the DNA content in each cancer cell using a flow cytometer and then analyzing the results. It can be predicted from the data shown in FIGS. 12(A) and 12(B), i.e., the cell cycle change observed for the control group (PBS(-) was used, FIG. 12(A)) and that observed for the experimental group (RF—NH$_2$ was used, FIG. 12(B)), that the pattern of the rat hepatoma cell cycle is differently affected by the presence and absence of the peptide.

Then the patterns observed in FIGS. 12(A) and 12(B) were examined in detail. In the G0/G1 stage, the DNA content is 2n, while that observed in the M stage is two times that observed for the G0/G1 stage or 4n. In the analysis of data shown in FIGS. 12(A) and 12(B), the DNA contents of 2n and 4n correspond to peaks or wide peaks at 360 and 700, respectively. If it is assumed that the analyzed pattern of the cell cycle change shown in FIGS. 12(A) and 12(B) comprises a linear coupling of peaks specific to G0/G1, S, M stages, the rate of cells in each stage can be obtained by dividing the pattern into these individual components. The results thus obtained are listed in the following Table 4.

TABLE 4

| | Rate of cells in Each Stage (%) | |
| --- | --- | --- |
| Cell Cycle Stage | Control Group (PBS(-) was added) | Experiment Group (DILRG-NH$_2$ was added) |
| G0/G1 Stage | 50.53 | 66.07 |
| S Stage | 37.55 | 21.84 |
| G2/M Stage | 11.92 | 12.10 |

As will be seen from the data shown in Table 4, the rates of cells in the G2 (preparatory stage for mitotic cell division) and the M stage (cell division stage) (corresponding to the G2/M stage in Table 4) of the cell cycle stages are 11.92% for the control group and 12.10% for the experimental group, which are almost identical to one another. On the other hand, the rates of cells in the G0 stage (resting stage) and in the G1 stage (DNA replication-determining stage) (corresponding to the G0/G1 stage in Table 4) are 50.53% for the control group and 66.07% for the experimental group. In other words, the rate for the experimental group is not less than 30% higher than that observed for the control group. Contrary to this, in the case of the S stage (DNA replication stage), the rates are 37.55% for the control group and 21.84% for the experimental group or the rate for the experimental group is not less than 40% lower than that observed for the control group. This result experimentally substantiates that the physiologically active substance of the present invention serves to extend the both G0 and G1 stages of the cell cycle, the S stage is accordingly shortened and thus the proliferation of the cells is inhibited.

Example 10

Relation between the Structure of the Physiologically Active Substance of the Present Invention and its Cell Growth-Inhibitory Effect The fact that the physiologically active substance derived from insects can results obtained in Examples 6, 7 and 8. In addition, as to the mechanism thereof, the results of Example 9 clearly demonstrate that the cell growth is inhibited through the control of the cell cycle. Thus, we investigated which part of the 5 amino acid sequence of this substance is indispensable to the cell growth-control activity from the structural standpoint. Cells were cultured by the same method used in Example 6. More specifically, in the control group, there were used a culture medium supplemented with PBS(-) and FMRF—$NH_2$(SEQ ID NO:4), which is widely distributed from echinoderms to insects and mammals, which comprises 4 amino acid residues and whose C-terminal is amidated. In an experimental group, there was used a culture medium supplemented with the complete synthetic peptide (DILRG—$NH_2$) or an incomplete synthetic peptide (ILRG—$NH_2$) free of the aspartic acid residue at the N-terminal in a concentration of 200 $\mu$g/$2.6\times10^5$ cells. The control group and the experimental group were cultured at 37° C. for 48 hours in the presence of 5% $CO_2$. Thereafter the cells were stained with trypan blue to thus determine the number of cells. The results thus obtained are shown in FIG. 13.

Figure 13:
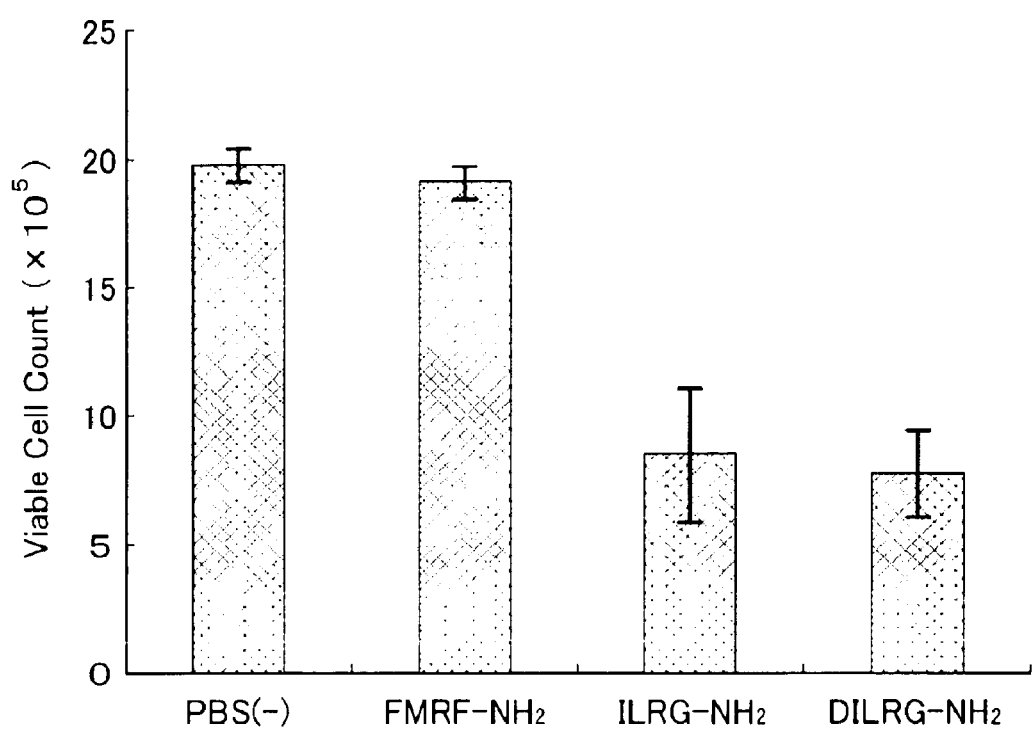
FIG. 13 is a graph showing the growth-control effect of DILRG—$NH_2$ (SEQ ID NO:5, the peptide of SEQ ID NO:1 having the C-terminal amidated) on the rat hepatoma cells (dRLh84), while comparing it with those observed for other substances.

As will be clear from the data shown in FIG. 13, in the control group in which the culture medium contained PBS (-) or FMRF—$NH_2$ (SEQ ID NO:4), the viable cell count ranges from 19.1 to $19.7\times10^5$, while the viable cell count observed for the experimental group in which the complete synthetic peptide is used is on the order of $7.7\times10^5$, this is one order of magnitude lower than that observed for the control group. In the case of the incomplete peptide free of the N-terminal, the viable cell count was found to be $8.4\times10^5$ cells, which is slightly greater than that observed for the complete peptide, but a sufficient growth-inhibitory effect was observed. Accordingly, it has been demonstrated that as a peptide possessing cell growth-control effect, ILRG whose C-terminal is amidated and free of the N-terminal aspartic acid residue is also effective. This result may be important information for the future development of stronger cell growth-inhibitory agents, while making the most use of a sequence having 4 to 5 amino acid residues as a leading compound.

Industrial Applicability

According to the dormancy-control substance comprising the gene Any-RF according to the present invention, the diapause termination of pre-larvae or the like can be controlled so as to extend or shorten the same by the administration of the dormancy-control substance, even if the growth of the pre-larvae or the like in dormancy is destined to awake from the dormancy. It would be expected that this peptide or the dormancy-control substance has diversified physiological activities and can be administered by a simple method.

Since the mechanism of the dormancy of insects has been elucidated according to the present invention, the low energy metabolism involved in the life mechanism, which is the essence of the dormancy of organisms, which have been confirmed to fall into dormancy, can be elucidated by applying the dormancy-control substance of the present invention to these organisms. This elucidation of the low energy metabolism will lead to the development of substances capable of maintaining the life of organisms over a long period of time in future and the dormancy-control substance of the present invention would ultimately become a leading compound for the development of life span-elongating substances.

In addition, the peptide of the present invention is a low molecular weight peptide, hardly causes any antigen-antibody reaction even if it is externally administered to a living body and possesses a specific growth-control activity. Therefore, the peptide can directly be administered to a variety of organisms, which fall into dormancy without any modification of the structure. In particular, the low molecular weight peptide of the present invention hardly serves as an antigen in the higher animals and therefore, the peptide synthesized has such an advantage that if it is externally administered to the living body, it would permit easy inspection and studies of the living body for any possible function.

The peptide or physiologically active substance according to the present invention is a penta-peptide comprising 5 amino acid residues (molecular weight: 570.595) or a tetra-peptide having 4 amino acid residues (molecular weight: 456.58), thus hardly causes any antigen-antibody reaction even when administered to a living body, unlike Cecropin (molecular weight: about 4 K) derived from silkworm and Pierisin (molecular weight: 98 K) derived from cabbage butterfly and possesses such a specific function as carcinostatic activity. Therefore, the peptide of the present invention is quite promising as a leading compound for the development of carcinostatic agents.

These peptides of the present invention can directly be administered to various kinds of animals without any modification. In other words, a low molecular weight peptide such as those of the present invention hardly serve as antigens not only to man, but also other higher animals such as domestic animals. Therefore, they have such an advantage that they show their carcinostatic functions when externally administered to a living body. Moreover, the peptide of the present invention may serve as a novel medicine free of any antigen-antibody reaction and having an excellent cell growth-control effect.

The low molecular weight peptide of the present invention, which is a physiologically active substance comprising the gene Any-RF, possesses a function of efficiently inhibiting any cancer cell-proliferation without accompanying any side effect. Therefore, the peptide of the present invention can efficiently control cell growth of, for instance, human hysterocarcinoma cells, hepatoma cells, lung cancer cells, gastric carcinoma cells and breast cancer cells and can thus efficiently perform biological cell-control. This physiologically active substance is greatly characterized in not only that it serves not to increase the number of living cancer cells (FIGS. 9, 10 and 11), but also that, with regard to the living cancer cells, it makes the cell cycle stage of the cancer cells change to thus temporarily convert them into quiescence or resting state. In this respect, the mechanism of action of the peptide of the present invention differs from those observed for any conventionally known carcinostatic agents and the peptide is quite useful as a medical product.

In other words, the physiologically active substance of the present invention also has such a function that it shortens the S stage corresponding to the DNA replication stage, while extending the G0 or testing stage and the G1 stage corresponding to the first stage. Contrary to this, either Cecropin or Pierisin induces apoptosis (cell death) of the cancer cells and as a result, it can simply inhibit cancer cell growth. Thus, the physiologically active substance of the present invention permits the solution of such a problem associated with the conventional carcinostatic agent including the foregoing Cecropin and Pierisin as the induction of apoptosis in the normal cells and the substance has an excellent effect such that it can inhibit only the growing cells without adversely affecting most of the normal cells in their resting stage and it can thus efficiently inhibit any proliferation of cancer cells.

In general, it has been said that the G0 and G1 stages of the differentiated and maturated normal cells require the longest period of time. Contrary to this, G0 and G1 stages of the cancer cells are in short period of time. The physiologically active substance of the present invention, which serves to elongate both of these stages, is fundamentally different from the conventionally reported cancer cell-control substances derived from insects. The conventional substances induce condensation and fragmentation of nuclei associated with the apoptosis and as a result, they can reduce the number of living cells. Contrary to this, the physiologically active substance of the present invention increases the G0 and G1 stages in the cell cycle, while reducing the stage and as a result, the cell cycle of the living cells is elongated to thus ultimately inhibit the cell growth. In other words, the physiologically active substance of the present invention does not induce any cell death, but controls the cell growth through the control of the cell cycle to thus suppress any increase of the number of cells.

As has been discussed above, the physiologically active substance of the present invention serves, as one of physiologically active functions, to extend the dormancy of pre-larvae of *Antheraea yamamai*. In general, the dormancy of organisms is recognized to be a state in which the proliferation of cells is interrupted and a low energy state is maintained. Therefore, as an example of wide variety of applications of this substance having diversified functions, it can be used for controlling the cancer cell growth in mammals. Moreover, the substance can inhibit any proliferation of a variety of biological cells and therefore, it can likewise be used as a long-term preservative for culture cells in cell level and individual organism.

What is claimed is:

1. A substantially purified nucleic acid encoding a pentapeptide consisting of an amino acid sequence of Asp-Ile-Leu-Arg-Gly (SEQ ID NO:1).

2. The substantially purified nucleic acid as set forth in claim 1, wherein the pentapeptide is obtained from pre-larvae of *Antheraea yamamai*.

3. A substantially purified dormancy-control pentapeptide having an amino acid sequence of Asp-Ile-Leu-Arg-Gly (SEQ ID NO:1), a molecular weight of 570.959 Da, and dormancy-control activity, wherein the C-terminal is amidated.

4. The dormancy-control pentapeptide as set forth in claim 3, wherein the dormancy-control pentapeptide is obtained from pre-larvae of *Antheraea yamamai*.

5. A method for preparing a dormancy-control pentapeptide, comprising the steps of
adding an acid-methanol solution consisting of methanol: water: acetic acid to pulverize pre-larvae of an insect;
triturating the resulting mixture;
centrifuging the mixture; and
subjecting the resulting supernatant to reverse phase high performance liquid chromatography and mixing-separation mode high performance liquid chromatography to give a dormancy-control pentapeptide, which has an amino acid sequence of Asp-Ile-Leu-Arg-Gly (SEQ ID NO:1) and a molecular weight of 570.959Da, wherein the C-terminal is amidated.

6. A composition comprising a physiologically acceptable carrier and, as an effective component, a pentapeptide having an amino acid sequence of Asp-Ile-Leu-Arg-Gly (SEQ ID NO:1) and a molecular weight of 570.959Da, wherein the C-terminal is amidated.

7. The composition as set forth in claim 6, wherein the pentapeptide is obtained from pre-larvae of *Antheraea yamamai*.

8. A composition comprising a physiologically acceptable carrier and, as an effective component, a tetrapeptide having an amino acid sequence of Ile-Leu-Arg-Gly (SEQ ID NO:2) and a molecular weight of 456.58Da, wherein the C-terminal is amidated.

9. The composition as set forth in claim 8, wherein the tetrapeptide is obtained from pre-larvae of *Antheraea yamamai*.

10. A substantially purified pentapeptide having an amino acid sequence of Asp-Ile-Leu-Arg-Gly (SEQ ID NO:1).

11. A substantially purified tetrapeptide an amino acid sequence of Ile-Leu-Arg-Gly (SEQ ID NO:2).

12. A substantially purified tetrapeptide having an amino acid sequence of Ile-Leu-Arg-Gly (SEQ ID NO:2), wherein the C-terminal is amidated.

* * * * *